US006251882B1

(12) United States Patent
Uckun et al.

(10) Patent No.: US 6,251,882 B1
(45) Date of Patent: Jun. 26, 2001

(54) ALKYL KETONES AS POTENT ANTI-CANCER AGENTS

(75) Inventors: Fatih M. Uckun, White Bear Lake; Rama Krishna Narla, St. Paul; David Alan Perry, Minneapolis, all of MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/352,647

(22) Filed: Jun. 29, 1999

Related U.S. Application Data
(60) Provisional application No. 60/090,997, filed on Jun. 29, 1998.

(51) Int. Cl.$^7$ .................. A61K 31/16; A61K 31/121; A61K 31/655; C07C 233/31; C07C 323/27

(52) U.S. Cl. .................. 514/150; 514/629; 534/564; 564/209; 564/215

(58) Field of Search .................. 534/564; 564/215, 564/209; 514/150, 629

(56) References Cited

U.S. PATENT DOCUMENTS 5,202,456 * 4/1993 Rando .................. 558/438

FOREIGN PATENT DOCUMENTS

| 05117169 | 5/1993 | (JP) . |
| WO 95/17512 | 6/1995 | (WO) . |
| WO 98/22098 | 5/1998 | (WO) . |

OTHER PUBLICATIONS

Chen, Y., Cancer Lett., Sep. 25, 1998, 13(2), 191–200 (Abstract).*
Chen et al., Biochemistry, 1996, 35, 3227–37.*
Chen, P. et al., "A Practical Method for the Preparation of α'–Chloroketones of N–Carbamate Protected–α–Aminoacids", *Tetrahedron Letters*, vol. 38, No. 18, pp. 3175–3178 (1997).
Inazu, T. et al., "Synthetic Studies on D–erytho–C18–sphingosine", *Noguchi Kenkyusho Jiho*, vol. 32, pp. 13–26, Abstract only (1989).
Jia, Z. et al., "Crystal Structures of Recombinant Rat Cathepsin B and a Cathepsin B–Inhibitor Complex", *The Journal of Biological Chemistry*, vol. 270, No. 10, pp. 5527–5533 (Mar. 10, 1995).
Albini, A. et al., "A Rapid in Vitro Assay for Quantitating the Invasive Potential of Tumor Cells", *Cancer Research*, vol. 47, No. 12, pp. 3239–3245 (Jun. 15, 1987).
Arceci, R. et al., "Clinical Significance of P–Glycoprotein in Multidrug Resistance Malignancies", *Blood*, vol. 81, No. 9, pp. 2215–2222 (May 1, 1993).
Au, L. et al., "Secretory Production of Bioactive Recombinant Human Granulocyte–Macrophage Colony–Stimulating Factor by a Baculovirus Expression System", *J. Biotechnol.*, vol. 51, No. 2, pp. 107–113 (Nov. 1, 1996).
Bendel, A. et al., "A Recombinant Fusion Toxin Targeted to the Granulocyte–Macrophage Colony–Stimulating Factor Receptor", *Leukemia & Lymphoma*, vol. 25, Nos. 3/4, pp. 257–270 (1997).
Bradford, M., "A Rapid and Sensitive Method for the Quantitation of Microgram Quantities of Protein Utilizing the Principle of Protein–Dye Binding", *Anal. Biochem.*, vol. 72, Nos. 1 and 2, pp. 248–254 (May 7, 1976).
Brocks, B. et al., "A TNF Receptor Antagonistic scFv, Which is not Secreted in Mammalian Cells, is Expressed as a Soluble Mono– and Bivalent scFv Derivative in Insect Cells", *Immunotechnology*, vol. 3, pp. 173–184 (1997).
Carbonetto, S., "The Extracellular Matrix of the Nervous System", *Trends in NeuroSciences*, pp. 382–387 (Oct. 1984).
Chan, H. et al., "Multidrug Resistance. Clinical Opportunities in Diagnosis and Circumvention", *Hematology/Oncology Clinics of North America*, vol. 8, No. 2, pp. 383–410 (Apr. 1994).
Chiou, C. et al., "Expression of Human Granulocyte–Macrophage Colony–Stimulating Factor Gene in Insect Cells by a Baculovirus Vector", *FEBS Letters*, vol. 259, No. 2, pp. 249–253 (Jan. 1, 1990).
Collins, S., "The HL–60 Promyelocytic Leukemia Cell Line: Proliferation, Differentiation, and Cellular Oncogene Expression", *Blood*, vol. 70, No. 5, pp. 1233–1244 (Nov. 1987).
Espevik, T. et al., "A Highly Sensitive Cell Line, WEHI 164 Clone 13, for Measuring Cytotoxic Factor/Tumor Necrosis Factor from Human Monocytes", *J. Immunological Methods*, vol. 95, pp. 99–105 (1986).
Frankel, A. et al., "IL2–Ricin Fusion Toxin is Selectively Cytotoxic in Vitro to IL2–Receptor–Bearing Tumor Cells", *Bioconjugate Chem.*, vol. 6, No. 6, pp. 666–672 (Nov./Dec. 1995).
Frankel, A. et al., "Characterization of a Ricin Fusion Toxin Targeted to the Interleukin–2 Receptor", *Protein Engineering*, vol. 9, No. 10, pp. 913–919 (Oct. 1996).
Fraser, A. et al., "A License to Kill", *Cell*, vol. 85, pp. 781–784 (Jun. 14, 1996).
Green, L. et al., "Rapid Colormetric Assay for Cell Viability: Application to the Quantitation of Cytotoxic and Growth Inhibitory Lymphokines", *J. Immunological Methods*, vol. 70, No. 1, pp. 257–268 (1984).
Griffiths, C. et al., "Production of Heterologous Proteins Using the Baculovirus/Insect Expression System", *Methods in Molecular Biology*, vol. 75, pp. 427–440 (1997).

(List continued on next page.)

*Primary Examiner*—Fiona T. Powers
(74) *Attorney, Agent, or Firm*—Merchant & Gould P.C.

(57) ABSTRACT

Novel alkyl ketone compounds having potent cytotoxic activity are described as anti-tumor agents and are particularly effective against leukemia and breast tumor cells.

22 Claims, 7 Drawing Sheets

OTHER PUBLICATIONS

Jean, L. et al., "Dipheria Toxin Receptor–Binding Domain Substitution with Interleukin 6: Genetic Construction and Interleukin 6 Receptor–Specific Action of a Diphtheria Toxin–Related Interleukin 6 Fusion Protein", *Protein Engineering*, vol. 4, No. 8, pp. 989–994 (Dec. 1991).

Jones, I. et al., "Baculovirus Vectors for Expression in Insect Cells", *Current Opinion in Biotechnology*, vol. 7, pp. 512–516 (1996).

Kool, M. et al., "Detection and Analysis of *Autographa californica* Nuclear Polyhedrosis Virus Mutants with Defective Interfering Properties", *Virology*, vol. 183, pp. 739–746 (1991).

Kretzschmar, T. et al., "High–level Expression in Insect Cells and Purification of Secreted Monomeric Single–chain Fv Antibodies", *J. Immunological Methods*, vol. 195, Nos. 1–2, pp. 93–101 (1996).

Langridge, J., "Extraction of Nucleic Acids from Agarose Gels", *Anal. Biochem.*, vol. 103, pp. 264–271 (1980).

Lakkis, F. et al., "Interleukin 4 Receptor Targeted Cytotoxicity: Genetic Construction and in vivo Immunosuppressive Activity of Diphtheria Toxin–Related Murine Interleukin 4 Fusion Protein", *Eur. J. Immunol.*, vol. 21, pp. 2253–2258 (Sep. 1991).

LeMaistre, C.F. et al., "Phase I Trial of an Interleukin–2 (IL–2) Fusion Toxin ($DAB_{486}IL–2$) in Hematologic Malignancies Expressing the IL–2 Receptor", *Blood*, vol. 79, No. 10, pp. 2547–2554 (May 15, 1992).

LeMaistre, C.F. et al., "Phase I Trial of a 90–Minute Infusion of the Fusion Toxin $DAB_{486}IL–2$ in Hematological Cancers", *Cancer Research*, vol. 53, No. 17, pp. 3930–3934 (Sep. 1, 1993).

LeMaistre, C.F. et al., "Phase I Trial of a Ligand Fusion–Protein ($DAB_{389}IL–2$) in Lymphomas Expressing the Receptor for Interleukin–2", *Blood*, vol. 91, No. 2, pp. 399–405 (Jan. 15, 1998).

Luckow, V. et al., "Efficient Generation of Infectious Recombinant Baculoviruses by Site–Specific Transposon–Mediated Insertion of Foreign Genes into a Baculovirus Genome Propagated in *Escherichia coli*", *J. Virology*, vol. 67, No. 8, pp. 4566–4579 (Aug. 1993).

McCarthy, N. et al., "Methods for Detecting and Quantifiying Apoptosis", *Current Topics in Developmental Biology*, vol. 36, pp. 259–278 (1998).

Medin, J. et al., "Efficient, Low–cost Protein Factories: Expression of Human Adenosine Deaminase in Baculovirus–infected Insect Larvae",*Proc. Natl. Acad. Sci. USA*, vol. 87, pp. 2760–2764 (Apr. 1990).

Meneghetti, C. et al., "Initial Clinical Experiences with an Interleukin–2 Fusion Toxin ($DAB_{486}$–IL–2)", *Genetically Engineered Toxins*, pp. 395–401 (Date Unknown).

Murhammer, D., "Review and Patents and Literature. The Use of Insect Cell Cultures for Recombinant Protein Synthesis: Engineering Aspects", *Applied Biochemistry and Biotechnology*, vol. 31, pp. 283–310 (1991).

Murphy, J. et al., "Genetic Construction, Expression, and Melanoma–Selective Cytotoxicity of a Diphtheria Toxin–Related α–Melanocyte–Stimulating Hormone Fusion Protein", *Proc. Natl. Acad. Sci. USA*, vol. 83, No. 21, pp. 8258–8262 (Nov. 1986).

Musto, P. et al., "High Risk of Early Resistant Relapse for Leukaemic Patients with Presence of Multidrug Resistance Associated P–Glycoprotein Positive Cells in Complete Remission", *British Journal of Haematology*, vol. 77, pp. 50–53 (1991).

Myers, D. et al., "Membrane–Associated CD19–LYN Complex is an Endogenous p53–Independent and Bcl–2–Independent Regulator of Apoptosis in Human B–Lineage Lymphoma Cells", *Proc. Natl. Acad. Sci. USA*, vol. 92, No. 21, pp. 9575–9579 (Oct. 1995).

Pennock, G. et al., "Strong and Regulated Expression of *Escherichia Coli* β–Galactosidase in Insect Cells wth a Baculovirus Vector", *Mol. Cell. Biol.*, vol. 4, No. 3, pp. 399–406 (Mar. 1984).

Perentesis, J. et al., "Granulocyte–Macrophage Colony–Stimulating Factor Receptor–Targeted Therapy of Chemotherapy –and Radiation–Resistant Human Myeloid Leukemias", *Leukemia and Lymphoma*, vol. 25, pp. 247–256 (1997).

Perentesis, J. et al., "Induction of Apoptosis in Multidrug–Resistant and Radiation–Resistant Acute Myeloid Leukemia Cells by a Recombinant Fusion Toxin Directed Against the Human Granulocyte Macrophage Colony–Stimulating Factor Receptor", *Clinical Cancer Research*, vol. 3, pp. 347–355 (Mar. 1997).

Perentesis, J. et al., "In Vivo Biotherapy of HL–60 Myeloid Leukemia with a Genetically Engineered Recombinant Fusion Toxin Directed Against the Human Granulocyte Macrophage Colony–Stimulating Factor Receptor", *Clinical Cancer Research*, vol. 3, pp. 2217–2227 (Dec. 1997).

Pirker, R. et al., "MDR1 Gene Expression and Treatment Outcome in Acute Myeloid Leukemia", *J. National Cancer Institute*, vol. 83, No. 10, pp. 708–712 (May 15, 1991).

Possee, R., "Baculoviruses as Expression Vectors", *Current Opinion in Biotechnology*, vol. 8, No. 5, pp. 569–572 (Oct. 1997).

Rivas, C. et al., "Expression of Granulocyte–Macrophage Colony–Stimulating Factor Receptors in Human Prostate Cancer", *Blood*, vol. 91, No. 3, pp. :1037–1043 (Feb. 1, 1998).

Rutka, J. et al., "The Extraceullar Matrix of the Central and Peripheral Nervous Systems: Structure and Function", *J. Neurosurg.*, vol. 69, No. 2, pp. 155–168 (Aug. 1988).

Sato, H. et al., "$MDR_1$ Transcript Levels as an Indication of Resistant Disease in Acute Myelogenous Leukaemia", *British Journal of Haematology*, vol. 75, pp. 340–345 (1990).

Schiffer, C., "Acute Myeloid Leukemia in Adults", *Cancer Medicine*, vol. 2, pp. 1907–1932 (1993).

Shaw, J. et al., "Cytotoxic Properties of $DAB_{486}EGF$ and $DAB_{389}EGF$, Epidermal Growth Factor (EGF) Receptor–targeted Fusion Toxins", *J. Bio. Chem.*, vol. 266, No. 31, pp. 21118–21124 (Nov. 5, 1991).

Steller, H., "Mechanisms and Genes of Cellular Suicide", *Science*, vol. 267, pp. 1445–1449 (Mar. 10, 1995).

Sudbeck, E. et al., "Structure–Based Design of Specific Inhibitors of Janus Kinase 3 as Apoptosis–Inducing Antileukemic Agents", *Clinical Cancer Research*, vol. 5, pp. 1569–1582 (Jun. 1999).

Thompson, C., "Apoptosis in the Pathogenesis and Treatment of Disease", *Science*, vol. 267, pp. 1456–1462 (Mar. 10, 1995).

Venstrom, K. et al., "Extraceullar Matrix 2: Role of Extracellular Matrix Molecules and their Receptors in the Nervous System", *The FASEB Journal*, vol. 7, pp. 996–1003 (Aug. 1993).

\* cited by examiner

ALKYL KETONES AS POTENT ANTI-CANCER AGENTS

This application claims the benefit of U.S. Provisional Application No. 60/090,997, filed Jun. 29, 1998.

FIELD OF THE INVENTION

The present invention relates to alkyl ketone compounds effective for treating tumor cells and particularly effective to induce apoptosis in leukemia cells, breast cancer cells, prostate cancer cells, and brain cancer cells.

BACKGROUND OF THE INVENTION

Cancer is a major disease that continues as one of the leading causes of death at any age.

In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

SUMMARY OF THE INVENTION

Novel alkyl ketone compounds have been found to be potent cytotoxic agents with potent activity against cancer cells. For example, certain alkyl ketone compounds were found to exhibit potent cytotoxic activity, particularly against human breast cancer and leukemic cell lines, at micromolar concentrations. These compounds were also effective in inhibiting adhesion and invasion by cancer cells.

Accordingly, the present invention includes novel compounds and compositions having potent cytotoxic activity. The present invention also includes methods for treating tumors by administering to a subject an effective amount of a compound of the invention to inhibit growth and/or induce apoptosis of tumor cells. Compositions of the invention contain an effective cytotoxic or inhibitory amount of a compound.

The compounds of the invention have the following formula I:

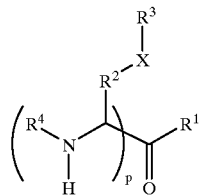

wherein p is an integer selected from 0 and 1;

X is O or S;

$R^1$ is H, hydroxyl, $(C_1-C_{30})$ alkyl, $(C_1-C_{30})$ alkenyl, $(C_1-C_{30})$ haloalkyl, $(C_1-C_{30})$ diazoalkyl, —$CH_2OC(O)R^5$, —$NR^6R^7$, or —$CH_2$—S—$R^9$ wherein $R^5$ is independently aryl, $(C_1-C_{30})$ alkyl, $(C_1-C_{30})$ haloalkyl, $(C_1-C_{30})$ alkenyl, $(C_1-C_{30})$ diazoalkyl, $(C_1-C_{24})$ cycloalkyl, or $(C_1-C_{24})$ cycloalkenyl, $R^6$ is independently H, $(C_1-C_{30})$ alkyl, $(C_1-C_{30})$ haloalkyl, $(C_1-C_{30})$ diazoalkyl, $(C_1-C_{30})$ alkenyl, $(C_1-C_{30})$ haloalkenyl, $(C_1-C_{24})$ cycloalkyl, or $(C_1-C_{24})$ cycloalkenyl;

$R^7$ is —$OR^8$, $R^8$ is independently $(C_1-C_{30})$ alkyl, $(C_1-C_{30})$ haloallyl, $(C_1-C_{30})$ diazoalkyl, $(C_1-C_{30})$ alkenyl, $(C_1-C_{30})$ haloalkenyl, $(C_1-C_{24})$ cycloalkyl, or $(C_1-C_{24})$ cycloalkenyl;

$R^9$ is independently $(C_1-C_{30})$ alkyl, $(C_1-C_{30})$ haloalkyl, $(C_1-C_{30})$ diazoalkyl, $(C_1-C_{30})$ alkenyl, $(C_1-C_{30})$ haloalkenyl, $(C_1-C_{24})$ cycloalkyl, $(C_1-C_{24})$ cycloalkenyl, or —$R^{10}CO_2H$;

$R^{10}$ is $(C_1-C_{30})$ alkyl or $(C_1-C_{30})$ alkenyl, $R^2$ is $C_1$ or $C_2$; $CH_2$ or $CH_2CH_2$ $R^3$ is $(C_1-C_{30})$ alkyl, $(C_1-C_{30})$ haloalkyl, $(C_1-C_{30})$ alkenyl, $(C_1-C_{30})$ haloalkenyl, $(C_1-C_{24})$ cycloalkyl, $(C_1-C_{24})$ cycloalkenyl, $(C_1-C_{24})$aryl, anthroquinonylmethyl, naphthylmethyl, —$SR^{11}$, or —$CR^{12}$;

$R^{11}$ is independently $(C_1-C_{30})$ alkyl, $(C_1-C_{30})$ haloalkyl, $(C_1-C_{30})$ alkenyl, or $(C_1-C_{30})$ haloalkenyl;

$R^{12}$ is aryl substituted methyl;

$R^4$ is H, —$C(O)R^3$, or —$C(O)$—$O$—$R^{14}$;

$R^{13}$ and $R^{14}$ are each independently $(C_1-C_{12})$ alkyl, $(C_1-C_{12})$ haloalkyl, $(C_1-C_{12})$ alkenyl, $(C_1-C_{12})$ haloalkenyl, $(C_3-C_{12})$ cycloalkyl, or $(C_3-C_{12})$ cycloalkenyl; or a pharmaceutically acceptable acid addition salt thereof.

Preferred compounds of the invention are those where p is the integer 1, $R^1$ is a haloalkyl, $R^2$ is $C_1$, $R^3$ is a $(C_1-C_{22})$ alkyl, and $R^4$ is acetyl. Most preferred is the compound N-Ac-S-dodecyl-Cys chloromethyl ketone (HI-131).

BRIEF DESCRIPTION OF THE DRAWINGS

FIG. 2A. NALM-6 control;

FIG. 2B. HI-131 treated NALM-6 cells;

FIG. 2C. UPN1 control;

FIG. 2D. HI-131 treated UPN1 cells;

FIG. 2E. UPN2 control;

FIG. 2F. HI-131 treated UPN2 cells.

DETAILED DESCRIPTION OF THE INVENTION

Figure 1A:
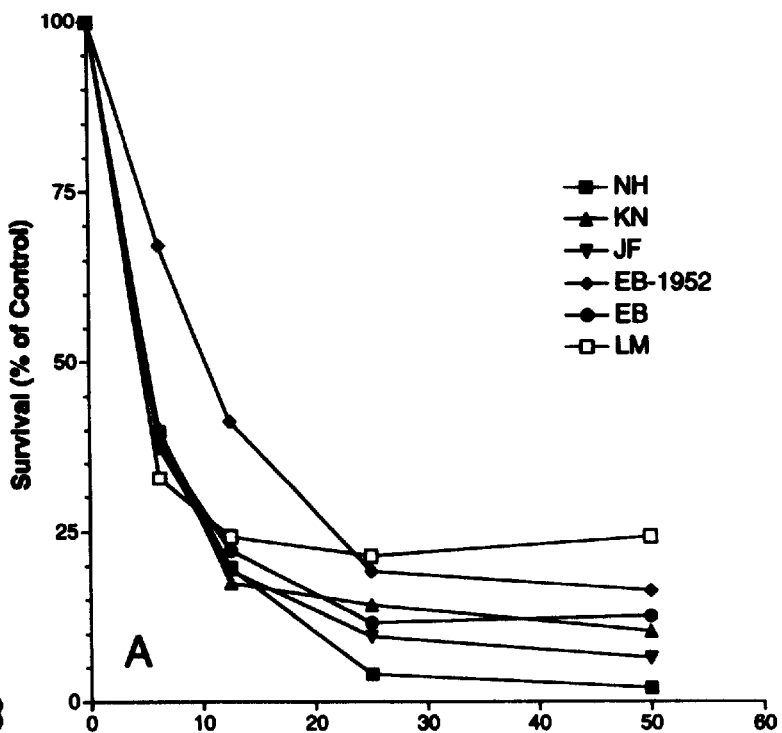
FIG. 1A is a graph showing survival of primary cancer cells taken from six children with leukemia and treated with different concentrations of compound HI-131 as a function of drug concentration.

The present invention includes novel alkyl ketone compounds having potent activity as cytotoxic agents. The compounds of the invention are useful agents for inhibiting growth or inducing apoptosis in tumor cells, for example, leukemia and breast tumor cells.

Definitions

All scientific and technical terms used in this application have meanings commonly used in the art unless otherwise specified. As used in this application, the following words or phrases have the meanings specified.

As used herein, "alkyl", includes both branched and straight-chain saturated aliphatic hydrocarbon groups having the specified number of carbon atoms. As a preferred embodiment, chains of 1 to 22 carbon atoms are included.

As used herein, "alkene", includes both branched and straight chain aliphatic hydrocarbon groups that have at least one double bond.

As used herein, "alkoxy", includes, saturated and unsaturated, branched and straight chain aliphatic hydrocarbon groups having a specified number of carbon atoms where at least one carbon atom forms a single-bond to an oxygen atom.

As used herein "amine", includes primary, secondary, and tertiary amines.

As used herein "halogen" or "halo" substituent includes fluoro, chloro, bromo, and iodo.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

"Substituted cycloalkyl" includes cyclic hydrocarbons having substituents including halo, alkyl, alkenyl, oxyalkyl, oxyalkenyl, haloalkyl, haloalkenyl, and aryl.

"Substituted cycloalkenyl" includes cyclic hydrocarbons having at least one double bond where substituents include halo, alkyl, alkenyl, oxyalkyl, oxyalkenyl, haloalkyl, haloalkenyl, and aryl.

"Substituted aryl" includes aromatic hydrocarbons having substituents including hydroxyl, amino, aminomethyl, halo, alkyl, alkenyl, oxyalkyl, oxyalkenyl, haloalkyl, haloalkenyl, and aryl.

"Treating" or "Treatment" in the context of this invention means the prevention or reduction in severity of symptoms or effects of a pathological condition, including prolonging life expectancy. In the context of cancer therapy, treatment includes prevention of tumor growth, reduction of tumor size, enhanced tumor cell death, and increased apoptosis.

COMPOUNDS OF THE INVENTION

The novel alkyl ketone compounds of the invention have the general structure represented by the following formula I:

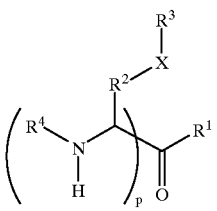

(I)

wherein p is 0 or 1;

X is O or S;

$R^1$ is H, hydroxyl, $(C_1-C_{30})$ alkyl, $(C_1-C_{30})$ alkenyl, $(C_1-C_{30})$ haloalkyl, $(C_1-C_{30})$ diazoalkyl, —$CH_2O$—$C(O)R^5$, —$NR^6R^7$, or —$CH_2$—$S$—$R^9$, wherein $R^5$ is independently aryl, $(C_1-C_{30})$ alkyl, $(C_1-C_{30})$ haloalkyl, $(C_1-C_{30})$ alkenyl, $(C_1-C_{30})$ diazoalkyl, $(C_1-C_{24})$ cycloalkyl, or $(C_1-C_{24})$ cycloalkenyl, $R^6$ is independently H, $(C_1-C_{30})$ alkyl, $(C_1-C_{30})$ haloalkyl, $(C_1-C_{30})$ diazoalkyl, $(C_1-C_{30})$ alkenyl, $(C_1-C_{30})$ haloalkenyl, $(C_1-C_{24})$ cycloalkyl, or $(C_1-C_{24})$ cycloalkenyl;

$R^7$ is —$OR^8$, $R^8$ is independently $(C_1-C_{30})$ alkyl, $(C_1-C_{30})$ haloalkyl, $(C_1-C_{30})$ diazoalkyl, $(C_1-C_{30})$ alkenyl, $(C_1-C_{30})$ haloalkenyl, $(C_1-C_{24})$ cycloalkyl, or $(C_1-C_{24})$ cycloalkenyl;

$R^9$ is independently $(C_1-C_{30})$ alkyl, $(C_1-C_{30})$ haloalkyl, $(C_1-C_{30})$ diazoalkyl, $(C_1-C_{30})$ alkenyl, $(C_1-C_{30})$ haloalkenyl, $(C_1-C_{24})$ cycloalkyl, $(C_1-C_{24})$ cycloalkenyl, or -$R^{10}CO_2H$;

$R^{10}$ is $(C_1-C_{30})$ alkyl or $(C_1-C_{30})$ alkenyl, $R^2$ is $C_1$ or $C_2$; $CH_2$ or $CH_2CH_2$ $R^3$ is $(C_{1-C30})$ alkyl, $(C_1-C_{30})$ haloalkyl, $(C_1-C_{30})$ alkenyl, $(C_1-C_{30})$ haloalkenyl, $(C_1-C_{24})$ cycloalkyl, $(C_1-C_{24})$ cycloalkenyl, $(C_1-C_{24})$aryl, anthroquinonylmethyl, naphthylmethyl, —$SR^{11}$, or —$CR^{12}$;

$R^{11}$ is independently $(C_1-C_{30})$ alkyl, $(C_1-C_{30})$ haloalkyl, $(C_1-C_{30})$ alkenyl, or $(C_1-C_{30})$ haloalkenyl;

$R^{12}$ is aryl substituted methyl;

$R^4$ is H, —$C(O)R^{13}$, or —$C(O$—$R^{14}$;

$R^{13}$ and $R^{14}$ are each independently $(C_1-C_{12})$ alkyl, $(C_1-C_{12})$ haloalkyl, $(C_1-C_{12})$ alkenyl, $(C_1-C_{12})$ haloalkenyl, $(C_3-C_{12})$ cycloalkyl, or $(C_3-C_{12})$ cycloalkenyl; or a pharmaceutically acceptable acid addition salt thereof.

The compounds of formula I are useful for the treatment of cancer, particularly the treatment of leukemia and breast cancer. In the method of the invention, a therapeutic amount of a compound of formula I is administered to a patient for the treatment of cancer.

A preferred compound of the invention has the structure of formula II:

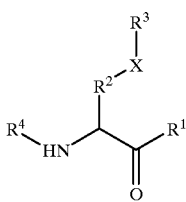

A preferred embodiment of the compound of Formula II is that shown as having formula III, where X is S, $R^3$ is dodecyl, and $R^4$ is acetyl:

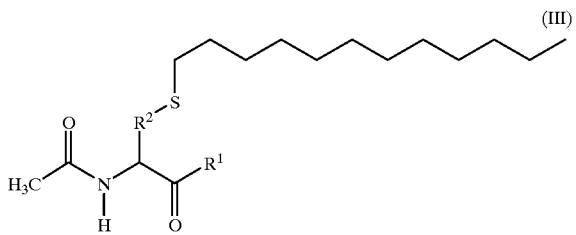

(III)

$R^1$ is most preferably chloromethyl; $R^2$ is preferably $CH_2$; $R^3$ is preferably a $C_{12}$ alkyl; $R^4$ is preferably acetyl; and X is preferably S. A most preferred compound of formula II is N-Ac-S-dodecyl-Cys chloromethyl ketone (HI-131).

Another embodiment of the invention is a compound of formula IV:

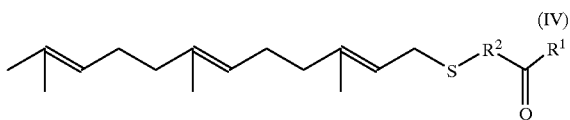

(IV)

Preferred compounds of the invention having potent anti-cancer affects are the following:

S-trans-trans-Farnesyl-mercaptoethyl diazomethyl ketone (HI-83);
N-Boc-S-farnesyl-Cys chloromethyl ketone (HI-124);
S-trans-trans-Farnesyl-2-mercaptoethyl chloromethyl ketone (HI-125);
N-Ac-S-(3-methyl-2-butenyl)-Cys chloromethyl ketone (HI-128);
N-Boc-S-dodecyl-Cys chloromethyl ketone (HI-129);
N-Boc-Gly-S-trans-trans-farnesyl-Cys chloromethyl ketone (HI-130);
N-Ac-S-dodecyl-Cys chloromethyl ketone (HI-131);
N-Ac-S-pentyl-cysteine chloromethyl ketone (HI-224);
N-Ac-S-pentadecyl-cysteine chloromethyl ketone (HI-225);
S-Dodecyl-Cys chloromethyl ketone hydrochloride (HI-252);
N-Ac-S-heptyl-cysteine chloromethyl ketone (HI-263);
N-Ac-S-dodecyl-Cys-H (HI-274);
N-Ac-S-methyl-cysteine chloromethyl ketone (HI-314);
N-Ac-S-undecyl-cysteine chloromethyl ketone (HI-321);
N-Ac-S-dodecyl-Cys diazomethyl ketone (HI-348);
N-Ac-S-trityl-cysteine chloromethyl ketone (HI-350);
N-Ac-S-octyl-cysteine chloromethyl ketone (HI-352);
N-Ac-S-tetradecyl-cysteine chloromethyl ketone (HI-354);
N-Ac-S-hexyl-cysteine chloromethyl ketone (HI-357);
N-Ac-S-butyl-cysteine chloromethyl ketone (HI-363);
N-Ac-S-nonyl-cysteine chloromethyl ketone (HI-364);
N-Ac-S-hexadecyl-cysteine chloromethyl ketone (HI-366);
N-Ac-S-trans-trans-farnesyl-Cys diazomethyl ketone (HI-367);
N-Ac-S-trans-trans-farmesyl-Cys chloromethyl ketone (HI-368);
N-Ac-S-propyl-cysteine chloromethyl ketone (HI-369);
N-Ac-S-decyl-cysteine chloromethyl ketone (HI-371);
N-Ac-S-benzyloxycarbonyl-cysteine chloromethyl ketone (HI-389);
N-Ac-S-2-naphthylmethyl-cysteine chloromethyl ketone (HI-392);
N-9-Fluorenylmethyloxycarbonyl-S-dodecyl-cysteine chloromethyl ketone (HI-398);
N-Ac-S-allyl-cysteine chloromethyl ketone (HI-419);
N-Ac-S-dodecyl-cysteine bromomethyl ketone (HI-488);
N-Ac-O-dodecyl-serine chloromethyl ketone (HI-489);
N-Trifluoroacetyl-S-dodecyl-cysteine chloromethyl ketone (HI-490);
N-Benzoyl-S-dodecyl-cysteine chloromethyl ketone (HI-491).

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose.

The free base forms differ from their respective salt forms somewhat in certain physical properties such as solubility in polar solvents, but the salts are otherwise equivalent to their respective free base forms for the purposes of the invention.

Cytotoxic Compounds

The compounds of the invention are effective cytotoxic agents, for example, against tumor cells such as leukemic and breast cancer cells. In the methods of the invention, the cytotoxic effects of alkyl ketone compounds are achieved by contacting cells, such as tumor cells, with micromolar amounts of the inhibitory compound. By way of example, a particularly useful anti-tumor agent is N-Ac-S-dodecyl-Cys chloromethyl ketone (HI-131) as shown in the Examples below.

Tumor Treatment

The compounds of the invention can be used in methods of tumor treatment, for example, by administering to a subject a compound of the invention in order to achieve an inhibition of tumor cell growth, a killing of tumor cells, induction of apoptosis, and/or increased patient survival time.

The cytotoxic compounds of the invention are suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homeostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane blebbing, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which is typically characterized, early-on by increased membrane permeability and cell rupture. As demonstrated in the Examples, the alkyl ketone compounds of the invention are effective agents for inducing apoptosis in tumor cells.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleageanous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption-for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. It can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When used in vivo to kill tumor cells, the administered dose is that effective to have the desired effect, such as sufficient to reduce or eliminate tumors. Appropriate amounts can be determined by those skilled in the art, extrapolating using known methods and relationships, from the in vitro data provided in the Examples.

In general, the dose of the novel alkyl ketone compounds effective to achieve tumor cell apoptosis, reduction in tumors, and increased survival time, is 1–100 mg/kg body weight/dose for a direct targeted administration.

The effective dose to be administered will vary with conditions specific to each patient In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the alkyl ketone compounds may be less than for single drug therapy.

EXAMPLES

The invention may be further clarified by reference to the following Examples, which serve to exemplify some of the embodiments, and not to limit the invention in any way.

Example 1

Synthetic procedure for Alkyl Ketones

The methods used to synthesize the alkyl ketone compounds beginning from readily available starting materials and ending with the desired compounds are described below.

The compounds contained within Table 1, Table 2, Table 3, and Table 6 were synthesized according to Schemes 1, 2, 3, and 4 illustrated below. In each scheme, a single compound is exemplified and used as a model to generally describe the synthesis. The specific synthesis of the other compounds is then discussed in detail.

The pathway used to synthesize the remaining compounds contained within Tables 3 and 6 and the compounds in Tables 4 and 5 are also described in detail below.

All chemicals were purchased from Aldrich Chemical Company (Milwaukee, Wisconsin) and used directly for synthesis without further purification. Anhydrous tetrahydrofuran was dried over sodium and distilled immediately prior to use. Column chromatography was performed using 230–400 mesh silica gel obtained from the Merck Company, with eluant as noted in the experimental procedure.

COMPOUNDS SYNTHESIZED ACCORDING TO SCHEME 1

The compounds (3a–e and 4a–e in Table 1; 3f, 4f, 3g, and 4g in Table 2) were prepared by the pathway exemplified in Scheme 1 for N-Ac-S-farnesyl-Cys chloromethyl ketone (HI-368) (4a).

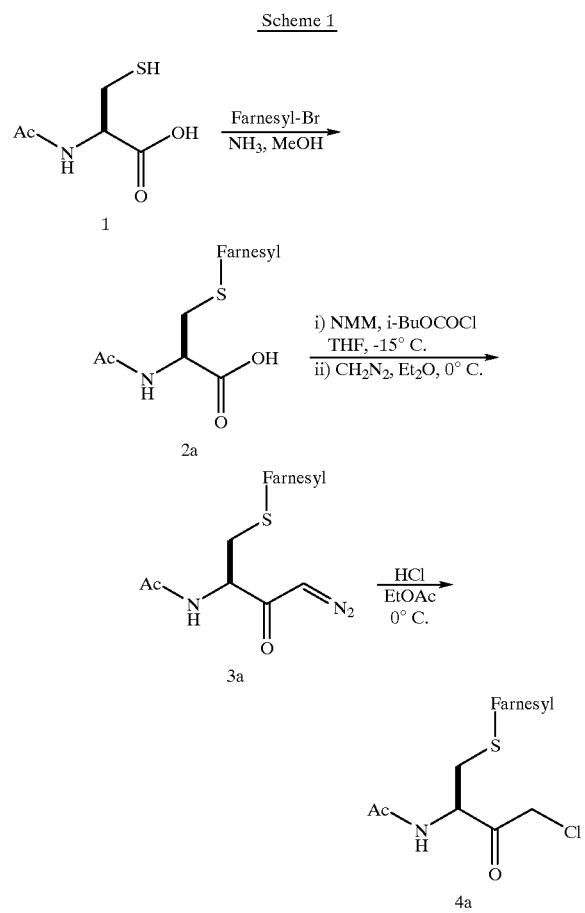

General description of the synthetic pathway illustrated in Scheme 1

The first step of scheme 1 was isoprenylation of the thiol group of N-Ac-Cys-OH by reaction of the appropriate isoprenyl bromide in a 4 M solution of ammonia in methanol according to the method of Brown and co-workers. This step was carried out in the presence of ethyl acetate when N-Ac-Cys-OH was dodecylated in order to solvate the bromododecane. In the second step, the S-alkylated acid (2a)

was activated as the mixed anhydride derivative using isobutylchloroformate and converted to the diazomethyl ketone (3a) by treatment with diazomethane. In the last step, the diazomethane was converted to the chloromethyl ketone (4a) with HCl in ethyl acetate at 0° C. for 10 minutes.

The chloromethyl compounds in Tables 1 and 2, 4a–4g, were made from the analogous diazomethyl compounds, 3a–3g, by replacement of the diazomethyl group with a chloromethyl group. The specific synthesis of each two member analogous group will therefore be considered together.

Specific methods used to synthesize the analogous pain of diazomethyl compounds using Scheme 1

1. N-Ac-S-trans-trans-farnesyl-Cys diazomethyl ketone (HI-367)(3a) and N-Ac-S-trans-trans-farnesyl-Cys chloromethyl ketone (HI-368)(4a)

Trans-trans -farnesyl bromide (1.57 g, 1.49 mL, 5.5 mmol) was added to N-Ac-Cys-OH (1) (0.82 g, 5 mmol) in 4 M ammonia in methanol (35 mL) at 0° C. The reaction was stirred at 0° C. for 3 h then at room temperature for 1 h. The solvent was removed under reduced pressure and the residue partitioned between 1-butanol and water. The butanol layer was dried (MgSO$_4$) and the solvent removed under reduced pressure. The residue was redissolved in methanol and washed with hexane. The methanol was then removed under reduced pressure to give N-Ac-S-trans-trans-farnesyl-Cys-OH (2a).

The N-Ac-S-trans-trans-farnesyl-Cys-OH (2a) (1.84 g, 5 mmol) produced in the previous step was dissolved in dry TBF (30 mL) and cooled to −15° C. 4-methyl morpholine (0.51 g, 0.55 mL, 5 mmol) and isobutyl chloroformate (0.68 g, 0.65 mL, 5 mmol) were added to the solution. The mixture was stirred at −15° C. for 5 minutes before being filtered by gravity into a solution of diazomethane in ethanolic ether (11 mmol, 30 mL) cooled in an ice bath. The resulting solution was stirred in ice for 3 h. Excess diazomethane was purged with nitrogen gas and the reaction mixture was washed with 5% sodium bicarbonate solution and water, dried over MgSO$_4$, and then the solvent was removed under reduced pressure. The product was purified by chromatography on silica gel (10–50% ethyl acetate in hexane) to give N-Ac-S-trans-trans-farnesyl-Cys diazomethyl ketone (3a).

A solution of HCl in ethyl acetate (1 M, 2 mL, 2 mmol) was added to a solution of the previously synthesized N-Ac-S-trans-trans-farnesyl-Cys diazomethyl ketone (3a) (1.57 g, 1 mmol) in ethyl acetate (10 mL) cooled in an ice bath. The reaction mixture was stirred at 0° C. for 5 to 10 min until the starting material was consumed by TLC. The solvent was then removed under reduced pressure and the residue purified by chromatography on silica gel (1:3 ethyl acetate:hexane) to give N-Ac-S-trans-trans-farnesyl-Cys chloromethyl ketone (4a).

2. N-Ac-S-trans-geranyl-Cys diazomethyl ketone (HI-122)(3c) and N-Ac-S-trans-geranyl-Cys chloromethyl ketone (HI-127)(4c)

N-Ac-S-trans-geranyl-Cys-OH (2c) was prepared as described above for N-Ac-S-trans-trans-farnesyl-Cys-OH (2a) except that trans-geranyl bromide was used instead of farnesyl bromide.

N-Ac-S-trans-geranyl-Cys diazomethyl ketone (M4 122) (3c) was prepared as described above for N-Ac-S-trans-trans-farnesyl-Cys diazomethyl ketone (3 a) except that N-Ac-S-trans-geranyl-Cys-OH (2c) (2.99 g, 10 mmol) was used instead of N-Ac-S-trans-trans-farnesyl-Cys-OH (2a). The crude material produced was purified by chromatography on silica gel (0–67% ethyl acetate in hexane) to give N-Ac-S-fans-geranyl-Cys diazomethyl ketone (HI 122) (3c).

N-Ac-S-trans-geranyl-Cys chloromethyl ketone (HI-127) (4c) was prepared as described above for N-Ac-S-trans-trans-farnesyl-Cys chloromethyl ketone (4a) except that N-Ac-S-trans-geranyl-Cys diazomethyl ketone (3c) (0.10 g, 0.3 mmol) was used instead of N-Ac-S-trans-trans-farnesyl-Cys diazomethyl ketone (3a). The crude material produced was purified by chromatography on silica gel (0–40% ethyl acetate in hexane) to give N-Ac-S-trans-geranyl-Cys chloromethyl ketone (HI-127) (4c).

3. N-Ac-S-(3-methyl-2-butenyl-Cys diazomethyl ketone (HI-123)(3d) and N-Ac-S-(3-methyl-2-butenyl)s chloromethyl ketone (HI-128)(4d)

N-Ac-S-(3-methyl-2-butenyl)-Cys-OH (2d) was prepared as described above for N-Ac-S-trans-trans-farnesyl-Cys-OH (2a) except that 4-bromo-2-methyl-2-butene was used instead of farnesyl bromide.

N-Ac-S-(3-methyl-2-butenyl)-Cys diazomethyl ketone (3d) was prepared as described above for N-Ac-S-trans-trans-farnesyl-Cys diazomethyl ketone (3a) except that N-Ac-S-(3-methyl-2-butenyl)-Cys-OH (2d) (0.69 g, 3 mmol) was used instead of N-Ac-S-trans-trans-farnesyl-Cys-OH (2a). The crude material was purified by chromatography on silica gel (0–5% methanol in methylene chloride) to give N-Ac-S-(3-methyl-2-butenyl)-Cys diazomethyl ketone (3d).

N-Ac-S-(3-methyl-2-butenyl)Cys chloromethyl ketone (4d) was prepared as described above for N-Ac-S-trans-trans-farnesyl-Cys chloromethyl ketone (4a) except that N-Ac-S-(3-methyl-2-butenyl)-Cys diazomethyl ketone (3d) (0.30 g, 1.2 mmol) was used instead of N-Ac-S-trans-trans-farnesyl-Cys diazomethyl ketone (3a). The crude product was purified by chromatography on silica gel (0–50% ethyl acetate in hexane) to give N-Ac-S(3-methyl-2-butenyl)-Cys chloromethyl ketone (4d).

4. N-Ac-S-dodecyl-Cys diazomethyl ketone (HI-348) (3e) and N-Ac-S-dodecyl-Cys chloromethyl ketone (HI-131) (4e)

N-Ac-Cys-OH (1.62 g, 9.9 mmol) and bromododecane (2.5 g, 10 mmol) were dissolved in a mixture of ethyl acetate (30 mL) and methanol (20 mL). A solution of NH$_3$ (4.2 M, 100 mL) in methanol was added at 0° C. and the reaction mixture was allowed to stir overnight at room temperature. The solvent was then removed under reduced pressure and the residue was partitioned between ethyl acetate and 1 M HCl. The organic layer was dried over MgSO$_4$ and the solvent removed under reduced pressure to give N-Ac-S-dodecyl-Cys-OH (2e).

N-Ac-S-dodecyl-Cys diazomethyl ketone (3e) was prepared as described above for N-Ac-S-trans- trans-farnesyl-Cys diazomethyl ketone (3a) except that N-Ac-S-dodecyl-Cys-OH (2e) (0.96 g, 2.9 mmol) was used instead of N-Ac-S-trans-trans-farnesyl-Cys-OH (2a). The crude product was purified by chromatography on silica gel (1:3 ethyl acetate/hexane) to give N-Ac-S-dodecyl-Cys diazomethyl ketone (3e).

N-Ac-S-dodecyl-Cys chloromethyl ketone (4e) was prepared as described above for N-Ac-S-farnesyl-Cys chloromethyl ketone (4a) except that N-Ac-S-dodecyl-Cys diazomethyl ketone (3e) (0.19 g, 0.5 mmol) was used instead of N-Ac-S-trans- trans-farnesyl-Cys diazomethyl ketone (3a). N-Ac-S-dodecyl-Cys chloromethyl ketone (4e) was obtained after removal of solvent.

5. N-Boc-S-farnesyl-Cys diazomethyl ketone (HI-82) (3b) and N-Boc-S-farnesyl-Cys chloromethyl ketone (HI-124) (4b)

These compounds were prepared using published literature procedures starting from L-cysteine.

13

6. S-trans-trans-Farnesyl-mercaptoethyl diazomethyl ketone (HI 83) (3f) and S-trans-trans-Farnesyl-2-mercaptoethyl chloromethyl ketone (HI 125) (4f)

3-(S-trans-trans-Farnesyl)-mercaptopropionic acid (2f) was prepared as described above for N-Ac-S-trans- trans-farnesyl-Cys-OH (2a) except that 3-mercaptopropionic acid was used instead of N-Ac-Cys-OH (1).

S-trans-trans-Farnesyl-mercaptoethyl diazomethyl ketone (3f) was prepared as described above for N-Ac-S-trans-trans-farnesyl-Cys diazomethyl ketone (3a) except that 3-(S-trans-trans-Farnesyl)-mercaptopropionic acid (2f) was used instead of N-Ac-S-trans-trans-farnesyl-Cys-OH (2a). The crude material was purified by chromatography on silica gel (1% MeOH in CHCl$_3$) to give S-trans-trans-Farnesyl-mercaptoethyl diazomethyl ketone (3f).

S-trans-trans-Farnesyl-2-mercaptoethyl chloromethyl ketone (HI 125) (4f) was prepared as described above for N-Ac-S-trans-trans-farnesyl-Cys chloromethyl ketone (4a) except that S-trans-trans-Farnesyl-mercaptoethyl diazomethyl ketone (3f) (0.52 g, 1.6 mmol) was used instead of N-Ac-S-trans-trans-farnesyl-Cys diazomethyl ketone (3a). The crude product was purified by chromatography on silica gel (0–10% ether in hexane) to give S-trans-trans-Farnesyl-2-mercaptoethyl chloromethyl ketone (HI 125) (4f).

7. S-trans-trans-Farnesyl-mercaptomethyl diazomethyl ketone (HI 84) (3g) and S-trans-trans-Farnesyl-mercaptomethyl chloromethyl ketone (HI 126) (4g) S-trans-trans-Farnesyl-mercaptoacetic acid (2g) was prepared as described above for N-Ac-S-trans-trans-farnesyl-Cys-OH (2a) except that mercaptoacetic acid was used instead of N-Ac-Cys-OH (1).

S-trans-trans-Farnesyl-mercaptomethyl diazomethyl ketone (3 g) was prepared as described above for N-Ac-S-trans-trans-farnesyl-Cys diazomethyl ketone (3a) except that S-trans-trans-Farnesyl-mercaptoacetic acid (2g) (0.71 g, 2.4 mmol) was used instead of N-Ac-S-trans-trans-farnesyl-Cys-OH (2a). The crude material was purified by chromatography on silica gel (0–100% CHCl$_3$ in hexane) to give S-trans-trans-Farnesyl-mercaptomethyl diazomethyl ketone (3g).

S-trans-trans-Farnesyl-mercaptomethyl chloromethyl ketone (4g) was prepared as described above for N-Ac-S-trans-trans-farnesyl-Cys chloromethyl ketone (4a) except that S-trans-trans-Farnesyl-mercaptomethyl diazomethyl ketone (3g) (0.58 g, 1.8 mmol) was used instead of N-Ac-S-trans-trans-farnesyl-Cys diazomethyl ketone (3a). The crude product was purified by chromatography on silica gel (0–10% ether in hexane) to give S-trans-trans-Farnesyl-mercaptomethyl chloromethyl ketone (4g).

COMPOUNDS SYNTHESIZED ACCORDING TO SCHEME 2

The synthesis of compounds 8 and 9 in Table 1 were prepared by the pathway exemplified in Scheme 2.

Scheme 2

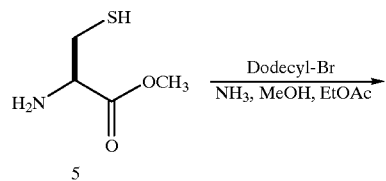

14

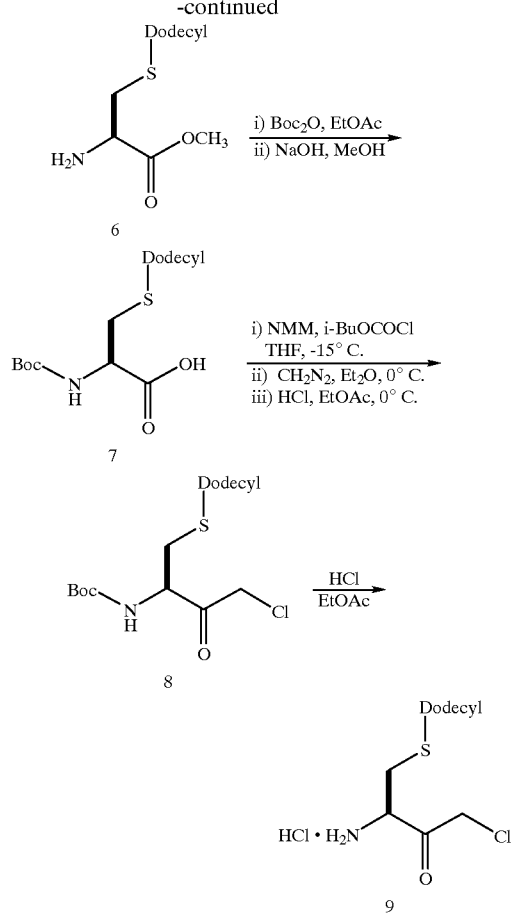

General description of the synthetic pathway illustrated in Scheme 2

The first step in scheme 2 was the dodecylation of cysteine methyl ester in a mixture of ethyl acetate and methanol. This was followed by Boc-protection, ester hydrolysis and conversion in turn to the chloromethyl ketone (8). S-Dodecyl-Cys chloromethyl ketone hydrochloride (9) was prepared from N-Boc-S-dodecyl-Cys chloromethyl ketone (8), by simply deprotecting the Boc group in a saturated solution of HCl in ethyl acetate.

Specific methods used to synthesize compounds using Scheme 2

8. N-Boc-S-dodecyl-Cys chloromethyl ketone (HI-129) (8) and S-Dodecyl-Cys chloromethyl ketone hydrochloride (HI-252) (9)

Ethyl acetate (30 mL) was added to a mixture of Cys-OCH$_3$ hydrochloride (1.71 g, 10 mmol) and bromododecane (2.5 g, 10 mmol) followed by addition of a solution of NH$_3$ (6.4 M) in methanol. The resulting cloudy suspension was allowed to stir overnight at room temperature and then the insoluble material was filtered off. The solution was concentrated and ethyl acetate (100 mL) was added. The solution was subsequently washed with water (3×40 mL) and dried over Na$_2$SO$_4$ to obtain S-Dodecyl-Cys-OCH$_3$ (6).

Di-tert-butyl dicarbonate (1.7 mL, 7.4 mmol) was added to a solution of the previously synthesized S-dodecyl-Cys-OCH$_3$ (6) (2.11 g, 7 mmol) in ethyl acetate at 0° C. The reaction mixture was allowed to stir for 4 h at room temperature. N-Boc-S-dodecyl-Cys-OCH$_3$ was obtained after removal of solvent.

A solution of NaOH (3 M, 3.6 mL, 10.8 mmol) was added to a solution of N-Boc-S-dodecyl-Cys-OCH₃ (3.42 g, 8.5 mmol) in methanol (80 mL) at 0° C. The reaction mixture was allowed to stir overnight at room temperature and then the solvent was removed under reduced pressure. Water (50 mL) was added to the residue and the aqueous solution, whose pH value was adjusted to 5, was washed with hexane (2×30 mL) and extracted with ethyl acetate (3×30 mL). The combined ethyl acetate fractions were dried over anhydrous Na₂SO₄ and the solvent removed under reduced pressure to give N-Boc-S-dodecyl-Cys-OH (7).

N-Boc-S-dodecyl-Cys diazomethyl ketone was prepared as described above for N-Ac-S-trans-trans-farnesyl-Cys diazomethyl ketone (3a) except that N-Boc-S-dodecyl-Cys-OH (7) (0.89 g, 2.3 mmol) was used instead of N-Ac-S-trans trans-farnesyl-Cys-OH (2a). The crude product was purified by chromatography on silica gel (1:2 ethyl acetate/hexane) to give N-Boc-S-dodecyl-Cys diazomethyl ketone.

N-Boc-S-dodecyl-Cys chloromethyl ketone (8) was prepared as described above for N-Ac-S-trans-trans-farnesyl-Cys chloromethyl ketone (4a) except that N-Boc-S-dodecyl-Cys diazomethyl ketone (0.56 g, 1.4 mmol) was used instead of N-Ac-S-trans-trans-farnesyl-Cys diazomethyl ketone (3a). N-Boc-S-dodecyl Cys chloromethyl ketone (8) was obtained upon removal of solvent.

The N-Boc-protected chloromethyl ketone (8) (0.21 g, 0.5 mmol) was dissolved in ethyl acetate (20 mL) and cooled in an ice bath. It was then saturated with dry HCl gas and the solution was stirred at room temperature until the starting material had disappeared by TLC (approx. 2 h). The solvent was removed under reduced pressure and the product, S-Dodecyl-Cys chloromethyl ketone hydrochloride (9), was obtained after recrystallization from ether.

COMPOUNDS SYNTHESIZED ACCORDING TO SCHEME 3

The compounds 12 and 13 in Table 1 were prepared by the pathway exemplified in Scheme 3.

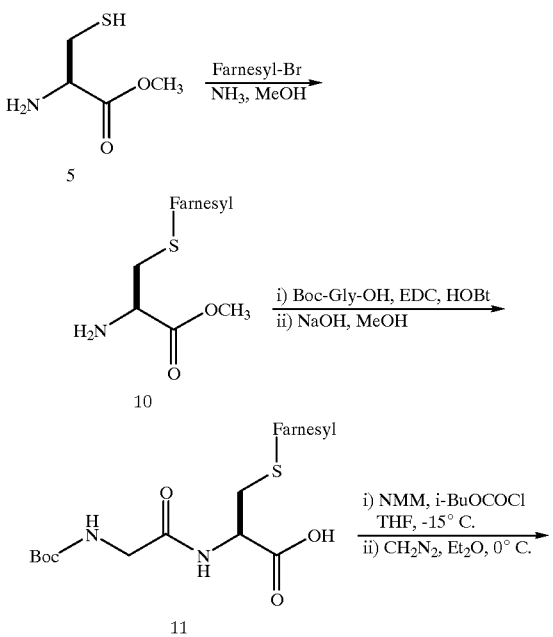

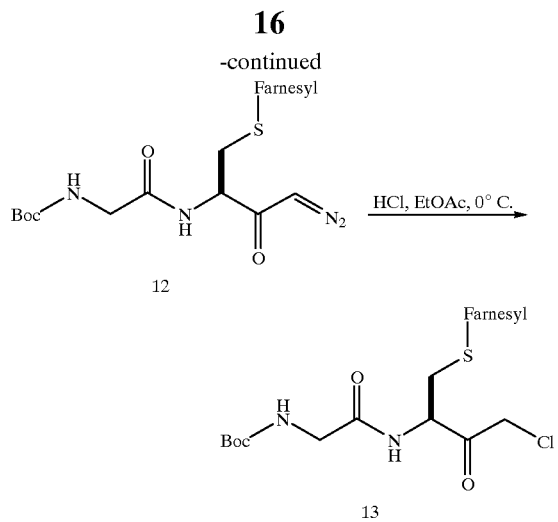

General description of the synthetic pathway illustrated in Scheme 3

The first step in scheme 3 was the farnesylation of cysteine methyl ester according to the method of Brown et al. The farnesylated cysteine methyl ester was then coupled with N-Boc-Gly-OH using EDC/HOBt. The ester was hydrolyzed to the acid (11) and the chloromethyl ketone prepared via the diazomethyl ketone (12).

Specific methods used to synthesize compounds using Scheme 3

9. N-Boc-Gly-S-trans-trans-farnesyl-Cys diazomethyl ketone (HI-401) (12) and N-Boc-Gly-S-trans-trans-farnesyl-Cys chloromethyl ketone (HI-130) (13)

A solution of ammonia (3.4 M, 80 mL) in methanol was added to a mixture of Cys-OCH₃ hydrochloride (1.72 g, 10 mmol) and trans trans-farnesyl bromide (2.85 g, 10 mmol) in methanol (30 mL) at 0° C. The reaction mixture was allowed to stir overnight at room temperature and then the solvent was removed under reduced pressure. The remaining residue was dissolved in ethyl acetate (100 mL) which had been washed with HCl (0.3 M), water, NaHCO₃ (6%) and dried over Na₂SO₄. The solvent was then removed under reduced pressure to give S-trans-trans-Farnesyl-Cys-OCH₃ (10).

DMF (30 mL) was added to a mixture of N-Boc-Gly-OH (1.3 g, 7.5 mmol), S-trans-trans-Farnesyl-Cys-OCH₃ (10) (1.28 g, 7.5 mmol) and HOBt (0.6 g, 4.4 mmol). The solution was cooled to 0° C. before the addition of EDC (1.52 g, 8.2 mmol) and the reaction mixture was stirred overnight at room temperature. The solvent was then removed under reduced pressure. The resulting residue was dissolved in ethyl acetate (60 mL) which had been washed with HCl (0.2 M), water, NaHCO₃ (6%) and dried over Na₂SO₄. Removal of the solvent under reduced pressure gave a yellow oil that was purified via chromatography on silica gel (1:1 ethyl acetate/hexane) to give pure N-Boc-Gly-S-trans-trans-farnesyl-Cys-OCH₃.

N-Boc-Gly-S-trans-trans-farnesyl-Cys-OCH3 (1.25 g, 2.52 mmol) was dissolved in methanol (70 mL) and then a solution of NaOH (3 M, 2.5 mL, 7.56 mmol) at 0° C. was added. The solution was stirred overnight at the same temperature. The solvent was then removed and the residue was dissolved in water (50 mL) that was subsequently acidified to pH 5. The aqueous solution was extracted with chloroform, the combined organic fractions were dried over anhydrous Na₂SO₄, and the solvent was removed under reduced pressure to give N-Boc-Gly-S-trans trans-farnesyl-Cys-OH (11).

N-Boc-Gly-S-trans trans-farnesyl-Cys diazomethyl ketone (12) was prepared as described above for N-Ac-S-trans-trans-farnesyl-Cys chloromethyl ketone (4a) except that N-Boc-Gly-S-trans-trans-farnesyl-Cys-OH (11) (0.39 g, 0.8 mmol) was used instead of N-Ac-S-trans-trans-farnesyl-Cys diazomethyl ketone (3a). The crude material was purified by chromatography on silica gel (1:3 ethyl acetate/hexane) to give N-Boc-Gly-S-trans-trans-farnesyl-Cys diazomethyl ketone (12).

N-Boc-Gly-S-trans trans-farnesyl-Cys chloromethyl ketone (13) was prepared as described above for N-Ac-S-trans trans-farnesyl-Cys chloromethyl ketone (4a) except that N-Boc-Gly-S-trans-trans-farnesyl-Cys diazomethyl ketone (0.21 g, 0.41 mmol) was used instead of N-Ac-S-trans-trans-farnesyl-Cys diazomethyl ketone (3a). N-Boc-Gly-S-trans-trans-farnesyl-Cys chloromethyl ketone (13) was obtained upon removal of solvent.

COMPOUNDS SYNTHESIZED ACCORDING TO SCHEME 4

The compounds 4h–4y in Table 3 and the compounds in Table 6 were prepared by the pathway exemplified in Scheme 4.

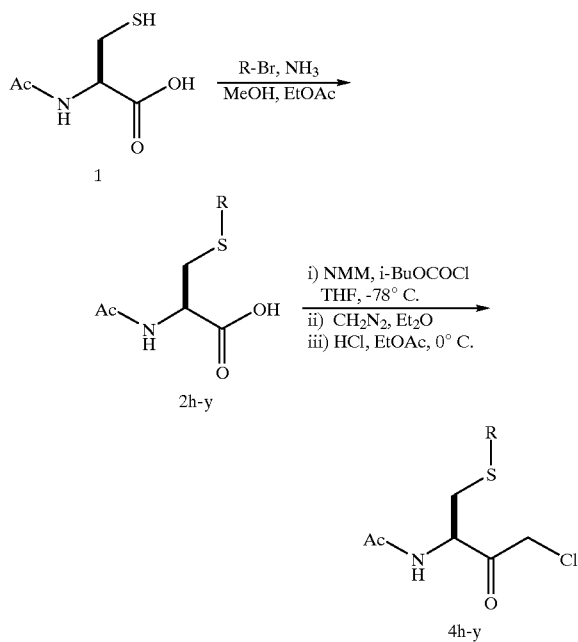

Scheme 4

Synthesis of the straight chain alkyl ketone derivatives (Tables 3 and 6) The straight chain alkyl ketone derivatives (4h–y) were synthesized by a modification of the standard literature procedure. Previously, the standard conditions for making diazomethyl ketones were used, but a closer study of the dodecyl derivative, N-Ac-S-dodecyl-Cys chloromethyl ketone (4e), showed significant formation of the methyl ester as a side-product. Presumably, the mixed anhydride intermediate either could not completely form or was hydrolyzed back to the acid before the diazomethane could react with it. Conducting the mixed anhydride formation at −78° C. increased the stability and longevity of the mixed anhydride and improved yield. Adding diazomethane directly to the solution at −78° C. without filtration led to over a three-fold improvement in yield from 15 to 55% for the dodecyl derivative, N-Ac-S-dodecyl-Cys chloromethyl ketone (4e), and gave a satisfactory yield of product for the majority of cysteine derivatives reported herein.

10. Specific methods used to synthesize the compounds of Table 3 and Table 6

The appropriate 1-bromoalkane (11 mmol) was added to a solution of N-Ac-Cys-OH (1.63 g, 10 mmol) in methanol (15 mL) and ethyl acetate (15 mL) that had been cooled in an ice bath. This was followed by the addition of a solution of ammonia in methanol (4M, 50 mL). The resulting solution was allowed to slowly warm to room temperature and was stirred overnight. The solvent was then removed under reduced pressure and the residue partitioned between ethyl acetate and 1M HCl. The layers were separated and the organic layer was dried over anhydrous $MgSO_4$. The solvent was removed under reduced pressure to give the desired N-Ac-S-alkyl-cysteine compound. An analytical sample of this could be obtained by recrystallization from ethyl acetate/hexane but was otherwise of sufficient purity to be used in further reactions.

NMM (0.20 g, 0.22 mL, 2 mmol) and isobutyl chloroformate (0.27 g, 0.26 mL, 2 mmol) was added to the desired N-Ac-S-alkyl-cysteine (2 mmol) in anhydrous THF (20 mL) that had been cooled to −78° C. The solution was then stirred at −78° C. for 20 min. A solution of diazomethane in ethanolic ether (10 mL) was carefully added and the solution allowed to slowly warm to room temperature. Further portions of diazomethane solution were added until a yellow color persisted. The solution was diluted with ether, washed with water and sodium bicarbonate solution and then dried over anhydrous $MgSO_4$. The solvent was removed under reduced pressure to yield the crude diazomethyl ketone compound.

The diazomethyl ketone was dissolved in ethyl acetate (20 mL) and cooled in an ice bath. A solution of HCl in ethyl acetate (2M, 2 mL) was added and the solution stirred in ice for 5 min until no more diazomethyl ketone could be observed by TLC. The solvent was removed under reduced pressure and the residue purified by chromatography on silica gel (ethyl acetate/hexane) to give the pure chloromethyl ketone compounds in Table 3 and Table 6.

11. Synthesis of the alkyl ketone compounds in Table 4

Synthesis of the compounds having variable $R^1$ groups shown in Table 4 was either by the method described above for HI-131, 348, and 208 or as follows. The bromomethyl ketone (HI-488) was synthesised from the diazomethyl ketone using HBr in a similar fashion to the chloromethyl ketone. The benzoyloxymethyl ketone (HI-508) was made starting from either the bromomethyl ketone or the chloromethyl ketone by displacement of the halogen with benzoic acid in the presence of potassium fluoride in DMF. The aldehyde (HI-274) was made from the acid (HI-208, 2e) via formation of the Weinreb amide (HI-267) by activation of the acid as its' mixed anhydride followed by coupling with N,O-dimethylhydroxylamine. The aldehyde was then synthesized by reduction of the Weinreb amide using $LiAlH_4$. The thiomethyl ketones (HI-269, 302, 399, 365 & 273) were made by displacement of the halogen of the bromo or chloromethyl ketones with the appropriate thiol in the presence of potassium carbonate in DMF.

12. Synthesis of the allyl ketone compounds in Table 5

The compounds varying the $R^4$ substituent (Table 5) were made either as noted above for HI-252, 131, and 129 or as follows. The majority of these compounds were made by reacting the appropriate acyl chloride or anhydride with the free amine compound (HI-252) in the presence of triethylamine. The dimethylaminobenzoyl derivative (HI-268) required activation of dimethylaminobenzoic acid as its mixed anhydride prior to reaction with the free amine. The serine derivative (HI-266) was synthesized by reaction of Boc-Ser-OH with sodium hydride and 1-bromododecane in DMF to give the N-Boc-O-dodecyl-Ser-OH and then with isobutylchloroformate/diazomethane and HCl in ethyl acetate at 0° C. as in the chemistry noted above. The acetyl serine derivative (HI-489) was synthesized from HI-266 by removal of the Boc group in saturated HCl in ethyl acetate followed by acetylation using acetic anhydride in dichloromethane in the presence of triethylamine.

EXAMPLE 2

Characterization of synthesized compounds

NMR spectra were recorded using a 300 MHz Varian instrument and the chemical shifts reported are in ppm based on tetramethylsilane as the internal standard. Chemical shifts for $^{13}$C NMR are referenced to the chloroform peak at 77.0 ppm. Melting points were done using a Fisher-Jones apparatus and are uncorrected. Fourier Transform Infra-red spectra were recorded on a FT-Nicolet model Protege 460 instrument. GC/MS analysis was done using a Hewlett-Packard GC/MS model 6890 with an HP5973 electron impact mass spectrometer. In addition, a Hewlett-Packard Matrix-Assisted Laser Desorption Ionization Time of Flight (MALDI-TOF) spectrometer model G2030A was used with cyano hydroxy benzoic acid as the matrix. Data are shown below.

N-Ac-S-trans-trans-farnesyl-Cys-OH (2a) Yellow oil. Yield 99%, 1.83 grams. $^1$H NMR (DMSO-d$_6$) δ 1.54 (s, 6H), 1.61 (s, 3H), 1.62 (s, 3I), 1.84 (s, 3H), 1.97 (m, 8H), 2.60 (dd, J=8.5, 13.7 Hz, 1H), 2.79 (dd, J=5.0, 13.7 Hz, 1H), 3.13 (m, 2H), 4.35 (m, 1H), 5.05 (m, 2H), 5.14 (t, J=7.8 Hz, 1H), 8.22 (d, J=8.2 Hz, 1H); $^{13}$C NMR (CDCl$_3$) δ 172.5, 169.5, 138.7, 134.8, 130.9, 124.3, 123.8, 120.4, 52.1, 48.8, 32.2, 29.0, 26.4, 26.1, 25.8, 22.6, 17.8, 16.1, 16.0; IR (KBr) 3334, 2966, 2922, 2854, 1732, 1659, 1543, 1441, 1377, 1219 cm$^{-1}$.

N-Ac-S-trans-geranyl-Cys-H (2c) Clear oil. Yield 97%, 2.92 g. $^1$H NMR (CDCl$_3$) δ 1.60 (s, 3H), 1.65 (s, 3H), 1.68 (s, 3H), 2.07 (m, 4H), 2.10 (s, 3H), 2.95 (ABX, J=3.6, 5.7, 13.2 Hz, 2H), 3.18 (d, J=6.9 Hz, 2H), 4.72 (m, 1H), 5.07 (m, 1H), 5.20 (t, J=7.9 Hz, 1H), 6.72 (br, 1H), 9.95 (br, 1H); $^{13}$C NMR (CDCl$_3$) δ 177.1, 139.9, 131.6, 123.7, 119.4, 52.6, 39.7, 33.0, 30.1, 29.8, 26.5, 25.8, 23.0, 20.9, 17.8, 16.2; IR (KBr) 3307, 2968, 2857, 2611, 1716, 1646, 1550, 1417, 1377, 1241 cm$^{-1}$; MS (MALDI-TOF) 323 (M+H+Na).

N-Ac-S-(3-methyl-2-butenyl)-Cys-OH (2d) Clear viscous oil. Yield 83%, 0.96 g. $^1$H NMR (CDCl$_3$) δ 1.66 (s, 3H), 1.73 (s, 3H), 2.07 (s, 3H), 2.95 (ABX, J=4.6, 6.2, 13.9 Hz, 2H), 3.17 (d, J=7.7 Hz, 2H), 4.65 (m, 1H), 5.20 (t, J=7.9 Hz, 1H), 7.28 (br, 1H), 8.25 (br, 1H); $^{13}$C NMR (CDCl$_3$) δ 174.1, 171.2, 136.1, 119.7, 52.7, 33.1, 30.1, 25.9, 25.8, 22.9, 17.8; IR (KBr) 3271, 3078, 2966, 2930, 2874, 1722, 1651, 1615, 1557, 1427, 1377, 1299, 1213, 1107, 1031 cm$^{-1}$.

N-Ac-S-dodecyl-Cys-OH (2e) White solid. Yield 98%, 3.23 g. m.p. 82–84° C. $^1$H NMR (CDCl$_3$) δ 0.88 (t, J=6.6 Hz, 3H), 1.26 (s, 20H), 1.57 (m, 2H), 2.09 (s, 3H), 2.55 (t, J=7.4 Hz, 2H), 3.03 (m, 2H), 4.75 (m, 1H), 6.40 (d, J=7.1 Hz, 1H); $^{13}$C NMR (CDCl$_3$) δ 168.3, 47.3, 28.8, 28.1, 27.3, 25.0, 24.9, 24.8, 24.6, 24.2, 18.4, 18.1, 9.6; IR (KBr) 3334, 2922, 2850, 1703, 1622, 1562, 1470, 1416, 1377, 1315, 1257, 1244 cm$^{-1}$; MS (MALDI-TOF) 332.7 (M+1).

3-S-trans-trans-Farnesyl)mercaptopropionic acid (2f) Clear oil. Yield 100%, 1.54 g. $^1$H NMR (CDCl$_3$) δ 1.60 (s, 6H), 1.66 (s, 3H), 1.68 (s, 3H), 2.03 (m, 8H), 2.60 (t, J=6.8 Hz, 2H), 2.72 (t, J=6.8 Hz, 2H), 3.17 (d, J=7.7 Hz, 2H), 5.09 (m, 2H), 5.22 (t, J=7.3 Hz, 1H), 8.77 (br, 1H); $^{13}$C NMR (CDCl$_3$) δ 162.9, 139.0, 135.2, 131.2, 124.2, 123.7, 120.0, 60.4, 39.75, 39.65, 36.8, 35.3, 31.7, 29.4, 26.8, 26.5, 26.1, 25.8, 17.8, 16.2, 16.1; IR (KBr) 3179, 2969, 2920, 2855, 1710, 1595, 1436, 1381, 1307 cm$^{-1}$.

S-trans-trans-Farnesyl-mercaptoacetic acid (2g) Clear oil. Yield 97%, 1.43 g. $^1$H NMR (CDCl$_3$) δ 1.60 (s, 6H), 1.66 (s, 3I), 1.68 (s, 3H), 2.03 (m, 8H), 3.19 (s, 2H), 3.30 (d, J=7.7 Hz, 2H), 5.09 (m, 2H), 5.21 (m, 1H), 8.95 (br, 1H); $^{13}$C NMR (CDCl$_3$) 176.5, 140.7, 135.3, 131.2, 124.2, 123.5, 118.9, 39.7, 39.6, 32.0, 30.0, 26.8, 26.4, 25.8, 17.8, 16.12, 16.09; IR (KBr) 3323, 2959, 2925, 2875, 1705, 1605, 1436, 1381, 1227, 1073, 1033 cm$^{-1}$.

N-Ac-S-trans-trans-farnesyl-Cys diazomethyl ketone (HI 367) (3a) Yellow oil. Yield 51%, 1 g. $^1$H NMR (CDCl$_3$) δ 1.60 (s, 6H), 1.67 (s, 3H), 1.68 (s, 3H), 2.03 (m, 8H), 2.05 (s, 3H), 2.82 (ABX, J=6.3, 6.6, 14.0 Hz, 2H), 3.20 (m, 2H), 4.64 (m, 11H), 5.09 (t, J=6.9 Hz, 2H), 5.22 (t, J=7.7 Hz, 1H), 5.58 (s, 1H), 6.51 (d, J=7.7 Hz, 1H); $^{13}$C (NRM (CDCl$_3$) δ 191.8, 169.7, 139.9, 135.3, 131.2, 124.2, 123.6, 119.5, 60.3, 55.2, 54.9, 39.65, 39.55, 33.1, 30.1, 26.7, 26.3, 25.7, 23.12 17.7, 16.1, 16.0; IR (KBr) 3290, 3057, 2966, 2920, 2854, 2108, 1651, 1533, 1441, 1375 cm$^{-1}$; GC/MS 363 (M–N$_2$).

N-Ac-S-trans-geranyl-Cys diazomethyl ketone (HI 122) (3c) Yellow oil. Yield 45%, 1.45 g. $^1$H NMR (CDCl$_3$) δ 1.60 (s, 3H), 1.67 (s, 3I), 1.68 (s, 3H), 2.05 (m, 7H), 2.82 (ABX, J=6.0, 6.3, 13.8 Hz, 2H), 3.20 (m, 2H), 4.64 (m, 1H), 5.08 (m, 2H), 5.22 (t, J=7.8 Hz 1H), 5.59 (s, 1H), 6.56 (d, J=7.2 Hz, 1H); $^3$C NMR (CDCl$_3$) δ 191.8, 169.7, 139.8, 131.6, 123.7, 119.5, 65.8, 55.3, 55.0, 39.6, 33.1, 30.2, 29.7, 26.5, 25.8, 23.2, 17.8, 16.2; GC/MS 295 (M–N$_2$); IR (KBr) 3300, 3061, 2965, 2924, 2856, 2107, 1732, 1651, 1538, 1455, 1373, 1260, 1111 cm$^{-1}$; MS (MALDI-TOF) 296.5 (M+H–N$_2$).

N-Ac-S-(3-methyl2-butenyly-Cys diazomethyl ketone (HI 123) (3d) Yellow oil. Yield 50%, 0.38 g. $^1$H NMR (CDCl$_3$) δ 1.68 (s, 3H), 1.75 (s, 3H), 2.05 (s, 3H), 2.82 (ABX, J=6.0, 6.3, 13.5 Hz, 2H), 3.18 (m, 2H), 4.64 (m, 1H), 5.21 (m, 1H), 5.59 (s, 1H), 6.58 (d, J=7.5 Hz, 1H); $^{13}$C NMR (CDCl$_3$) δ 191.7, 169.6, 136.1, 119.7, 55.3, 54.9, 52.7, 52.6, 51.8, 37.7, 33.2, 30.3, 30.1, 25.7, 25.6, 23.1, 19.1, 17.8; GC/MS 227 (M–N$_2$); IR (KBr) 3296, 3062, 2970, 2928, 2108, 1745, 1667, 1548, 1441, 1373, 1145, 1039 cm$^{-1}$; MS (MALDI-TOF) 278.6 (M+Na), 256.3 M+H), 250.4 (M+Na–N$_2$), 228.3 (M+H–N$_2$).

N-Ac-S-dodecyl-Cys diazomethyl ketone (HI 348) (3e) Off-white solid. Yield 15%, 0.16 g. m.p. 45–48° C. $^1$H NMR (CDCl$_3$) δ 0.88 (t, J=6.7 Hz, 3H), 1.25 (m, 18H), 5.59 (s, 1H), 2H), 2.05 (s, 3H), 2.55 (t, J=7.4 Hz, 2H), 2.88 (d, J=6.3 Hz, 2H), 4.62 (m, 1H), 5.59 (s, 1H), 6.40 (d, J=7.1 Hz, 1H; $^{13}$C NMR (CDCl$_3$) δ 191.8, 169.8, 55.4, 55.0, 34.1, 32.9, 32.8, 31.9, 29.6, 29.5, 29.4, 29.3, 29.2, 28.8, 28.2, 23.2, 22.7, 14.14; IR (KBr) 3287, 3068, 2919, 2853, 2126, 1655, 1547, 1383, 1168, 725 cm$^{-1}$.

S-trans-trans-Farnesyl-mercaptoethyl diazomethyl ketone (HI 83) (31) Yellow oil. Yield 45%, 0.45 g. $^1$H NMR (CDCl$_3$) δ 1.60 (s, 6H), 1.67 (s, 3H1), 1.68 (s, 3H), 2.03 (m, 8H), 2.58 (t, J=7.2 Hz, 2H), 2.75 (t, J=7.2 Hz, 2H), 3.17 (d, J=7.7 Hz, 2H), 5.09 (m, 2H), 5.24 (t, J=7.3 Hz, 1H), 5.29 (s, 1H); $^{13}$C NMR (CDCl$_3$) δ 139.1, 135.2, 131.2, 124.2, 123.6, 120.0, 68.1, 51.8, 39.7, 39.6, 38.7, 34.8, 30.4, 29.8, 29.4, 26.8, 26.5, 26.0, 25.8, 17.8, 16.2, 16.1; IR (KBr) 3095, 2967, 2922, 2855, 2105, 1715, 1645, 1445, 1368, 1318 cm$^{-1}$; MS (MALDI-TOF) 357 (M +Na).

S-trans-trans-Farnesyl-mercaptomethyl diazomethyl ketone (HI 84) (3g) Yellow oil. Yield 47%. 0.36 g. $^1$H NMR (CDCl$_3$) δ 1.60 (s, 6H), 1.66 (s, 3H), 1.68 (s, 3H), 2.03 (m, 8H), 3.20 (m, 4H), 5.09 (m, 2H), 5.20 (t, J=7.8 Hz, 1H), 5.77 (s, 1 H); $^{13}$C NMR (CDCl$_3$) δ 140.6, 135.3, 131.2, 124.2, 123.6, 118.9, 54.1, 47.2, 39.8, 39.7, 38.8, 31.9, 30.0, 39.8, 26.8, 26.6, 26.4, 25.8, 17.8, 16.2, 16.15; IR(KBr) 3107, 2966, 2923, 2854, 2105, 1724, 1639, 1449, 1355cm$^{-1}$, MS (MALDI-TOF) 343 (M+Na).

N-Ac-S-trans-trans-farnesyl-Cys chloromethyl ketone (HI 368) (4a) Pale yellow solid. Yield 55%, 0.22 grams, m.p. 59–61° C. $^1$H NMR (CDCl$_3$) δ 1.56 (s, 6H), 1.64 (s, 6H), 2.01 (s, 3H), 2.04 (m, 8H), 2.85 (ABX, J=5.8, 6.6, 13.9 Hz, 2H), 3.14 (m, 2H), 4.31 (s, 2H), 4.85 (m, 1H), 5.05 (t, J=6.9 Hz, 2H), 5.17 (t, J=7.7 Hz, 1H), 6.36 (br, 1H); $^{13}$C NMR (CDCl$_3$) δ 199.9, 170.0, 140.5, 135.4, 131.3, 124.2, 123.5, 119.2, 60.4, 55.3, 47.3, 39.7, 39.6, 31.9, 29.9, 26.7, 26.4, 25.7, 22.9, 17.7, 16.2, 16.0; IR (KBr) 3300, 3061, 2926, 2852, 2825, 1738, 1633, 1541, 1448, 1421, 1371, 1286, 1078 cm$^{-1}$; GC/MS 363 (M–HCl).

N-Ac-S-trans-geranyl-Cys chloromethyl ketone (HI 127) (4c) Yellow oil. Yield 27%, 0.03 g. $^1$H NMR (CDCl$_3$) δ 1.61 (s, 3H), 1.67 (s, 3H), 1.68 (s, 3H), 2.05 (s, 3H), 2.07 (m, 4H), 2.88 (ABX, J=5.9, 6.3, 13.7 Hz, 2H), 3.18 (m, 2H), 4.34 (m, 2H), 4.89 (q, J=6.3 Hz, 1H), 5.07 (m, 1H), 5.21 (t, J=7.8 Hz, 1H); °C NMR (CDCl$^1$) δ 199.8, 169.9, 140.4, 131.8, 123.6, 119.2, 55.3, 47.3, 39.7, 39.6, 32.0, 30.0, 29.8, 26.5, 25.8, 23.0, 17.8, 16.3; IR (KBr) 3342, 2970, 2926, 2859, 1741, 1732, 1664, 1651, 1538, 1446, 1379, 1301, 1084 cm$^{-1}$; GC/MS 295 (M–Cl), 205 (farnesyl).

N-Ac-S-(3-methyl2-butenyl-Cys chloromethyl ketone (HI 128) (4d) Off-white solid. Yield 56%, 0.18 g. $^1$H NMR (CDCl$_3$) δ 1.68 (s, 3H), 1.76 (s, 3H), 2.06 (s, 3H), 2.89 (ABX, J=6.0, 6.5, 13.8 Hz, 2H), 3.17 (m, 2H), 4.34 (m, 2H), 4.89 (q, J=6.3 Hz, 1H), 5.20 (t, J=7.8 Hz, 1H), 6.32 (d, J=5.5 Hz, 1H); $^{13}$C NMR (CDCl$_3$) δ 199.8, 169.9, 136.8, 119.4, 55.4, 47.3, 32.1, 30.2, 25.8, 23.0, 17.9; IR (KBr) 3302, 3060, 2976, 2958, 2927, 2853, 1738, 1635, 1541, 1423, 1371, 1286, 1216, 1078 cm$^{-1}$; GC/MS 227 (M–Cl).

N-Ac-S-dodecyl-Cys chloromethyl ketone (HI 131) (4e) Pale yellow solid. Yield 100%, 0.18 g. m.p. 73–74° C. $^1$H NMR (CDCl$_3$) δ 0.88 (t, J=6.7 Hz, 3H), 1.26 (m, 18H), 1.57 (m, 2H), 2.06 (s, 3H), 2.54 (t, J=7.3 Hz, 2H), 2.94 (ABX, J=6.0, 6.3, 13.9 Hz, 2H), 4.35 (m, 2H), 4.91 (m, 1H), 6.31 (br, 1H); $^{13}$C NMR (CDCl$_3$) δ 195.2, 165.3, 50.8, 42.7, 29.6, 28.4, 28.2, 27.3, 25.1, 25.0, 24.9, 24.83, 24.8, 24.7, 24.5, 24.1, 18.3, 18.1, 9.5; IR (KBr) 3302, 2924, 2854, 45 1738, 1660, 1537, 1456, 1377, 1261, 1165, 1095, 1040 cm$^{-1}$; MS (MALDI-TOF), 364.9 (M+1), 328.9 (M–Cl).

S-trans-trans-Farnesyl-2-mercaptoethyl chloromethyl ketone (HI 125) (4f) Yellow oil. Yield 68%, 0.36 g. $^1$H NMR (CDCl$_3$) δ 1.60 (s, 6H), 1.67 (s, 3H), 1.68 (s, 3H), 2.03 (m, 8H), 2.74 (t, J=6.6 Hz, 2H), 2.89 (t, J=6.6 Hz, 2H), 3.18 (d, J=7.5 Hz, 2H), 4.10 (s, 2H), 5.09 (m, 2H), 5.23 (t, J=7.8 Hz, 1H); $^{13}$C NMR (CDCl$_3$) δ 200.9, 139.2, 135.3, 131.2, 124.2, 123.6, 120.0, 48.3, 40.1, 39.7, 39.6, 29.8, 26.8, 26.5, 25.8, 24.8, 17.8, 16.2, 16.1; IR (KBr) 2964, 2925, 2852, 1726, 1441, 1379, 1351, 1110, 1077 cm$^{-1}$; GC/MS 342 (M), 307 (M–Cl), 205 (farnesyl); MS (MALDI-TOF) 342.6 (M$^+$).

S-trans-trans-Farnesyl-mercaptomethyl chloromethyl ketone (HI 126) (4g) Clear oil. Yield 17%, 0.10 g. $^1$H NMR (CDCl$_3$) δ 1.60 (s, 6H), 1.66 (s, 3H), 1.68 (s, 3H), 2.03 (m, 8H), 3.16 (d, J=7.8 Hz, 2H), 3.34 (s, 2H), 4.34 (s, 2H), 5.09 (m, 2H), 5.18 (m, 1H); $^{13}$C NMR (CDCl$_3$) δ 197.2, 140.9, 135.3, 131.1, 124.1, 123.6, 118.6, 46.2, 39.7, 39.6, 38.4, 37.4, 37.1, 32.0, 31.8, 29.8, 26.7, 26.5, 26.3, 25.3, 17.7, 16.2, 16.1; IR (KBr) 3444, 2965, 2926, 2859, 1732, 1712, 1664, 1446, 1384, 1243, 1108 cm$^{-1}$; GC/MS 328 (M$^+$), 294 (M–Cl), 205 (farnesyl).

S-Dodecyl-Cys-OCH$_3$ (6) Light yellow oil. Yield 61%, 1.85 g. $^1$H NMR (CDCl$_3$) δ 0.88 (t, J=6.6 Hz, 3H), 1.26 (s, 20H), 2.53 (t, J=7.5 Hz, 2H), 2.76 (m, 1H), 3.67 (m, 1H), 3.75 (s, 3H); IR (KBr) 3381, 2924, 2854, 1743, 1466, 1437, 1196, 1175 cm$^{-1}$; GC/MS 303 (M$^+$).

N-Boc-S-dodecyl-Cys-OCH$_3$ Clear oil. Yield 100%, 2.82 g. $^1$H NMR (CDCl$_3$) δ 0.88 (t, J=7.1 Hz, 3H), 1.25 (s, 20H), 1.45 (s, 9H), 2.51 (t, J=7.5 Hz, 2H), 2.95 (d, J=5.2 Hz, 1H), 3.76 (s, 3H), 4.52 (m, 1H), 5.37 (m, 1H); IR (KBr) 2977, 2932, 1814, 1759, 1062 cm$^{-1}$; GC/MS 403 (M$^+$), 286, 215, 57.

N-Boc-S-dodecyl Cys-OH (7) Yellow oil. Yield 80%, 2.65 g. $^1$H NMR (CDCl$_3$) δ 0.88 (t, J=6.6 Hz, 3H), 1.24 (m, 20H), 1.45 (s, 9H), 2.52 (t, J=7.4 Hz, 2H), 2.96 (d, J=4.9 Hz), 2H), 4.50 (m, 1H), 5.38 (br, 1H); $^{13}$C NMR (CDCl$_3$) δ 175.0, 156.0, 80.0, 53.0, 34.5, 34.1, 32.9, 32.6, 32.0, 29.7, 29.6, 29.4, 29.2, 28.8, 28.2, 22.8, 14.0; IR (KBr) 3328, 2922, 2852, 1719, 1503, 1368, 1172, 1052cm$^{-1}$.

N-Boc-S-dodecyl-Cys diazomethyl ketone Light yellow oil that solidified upon standing. Yield 59%, 0.56 g. $^1$H NMR (CDCl$_3$) δ 0.88 (t, J=6.7 Hz, 3H), 1.26 (s, 18H), 1.46 (s, 9H), 1.58 (m, 2H), 2.53 (m, 2H), 2.89 (m, 2H), 4.30 (m, 1H), 5.61 (br, 1H); IR (KBr) 3323, 2924, 2853, 2108, 1718, 1647, 1499, 1369, 1168 cm$^{-1}$; MS (MALDI-TOF) 386.5 (M–N$_2$).

N-Boc-S-dodecyl-Cys chloromethyl ketone (HI 129) (8) Clear oil that solidified upon standing. Yield 100%, 0.57 g. m.p. 43–49° C. $^1$H NMR (CDCl$_3$) δ 0.88 (m, 3H), 1.26 (s, 18H), 1.45 (s, 9H), 1.57 (m, 2O), 2.53 (m, 2H), 2.93 (m, 2H), 4.37 (s, 1H), 4.60 (m, 1H), 5.37 (br s, 1H); $^{13}$C (CDCl$_3$) δ 172.5, 130.8, 56.9, 53.2, 52.5, 47.4, 34.5, 33.2, 32.9, 32.8, 32.0, 29.7, 29.6, 29.5, 29.4, 29.2, 28.8, 28.6, 28.3, 28.0, 22.8, 14.2; IR (KBr) 3363, 2926, 2854, 1713, 1497, 1468, 1367, 1252, 1167 cm$^{-1}$.

S-Dodecyl-Cys chloromethyl ketone hydrochloride (HI 252) (9) Silver-white solid. Yield 81%, 0.14. m.p. 118–119° C. (decomp.). $^1$H NMR (DMSOd$_6$) δ 0.84 (t, J=6.7 Hz, 3H), 1.23 (m, 18H), 1.51 (m, 2H), 2.57 (t, J=7.3 Hz, 2H), 2.96 (dd, J=6.9, 14.4 Hz, 1H), 3.09 (dd, J=5.8, 14.4 Hz, 11H), 4.44 (t, J=6.2 Hz, 1H), 4.84 (m, 2H), 8.58 (br, 3H); $^{13}$C NMR (DMSO-d$_6$) δ 193.2, 51.4, 43.9, 27.3, 27.1, 26.2, 24.9, 24.6, 24.4, 24.0, 18.0, 9.8; IR (KBr) 2953, 2922, 2852, 1738, 1470, 1385, 1149cm$^{-1}$.

S-trans-trans-Farnesyl-Cys-OCH$_3$ (10) Clear oil. Yield 68%, 2.31 g. $^1$H NMR (CDCl$_3$) δ 1.59 (s, 6H), 1.67 (s, 6H), 2.08 (m, 8H), 2.68 (dd, J=7.7, 13.5 Hz, 1H), 2.89 (dd, J=4.8, 13.5 Hz, 1H), 3.19 (m, 2H), 3.61 (m, 1H), 3.75 (s, 3H), 5.08 (m, 2H), 5.21 (t, J=7.9 Hz, 1H); IR (KBr) 3348, 3376, 3314, 2978, 2922, 2860, 1746, 1684, 1452, 1395, 1209, 1168, 843 cm$^{-1}$; GC-MS 339 (M$^+$), 270, 202, 135, 81, 69.

N-Boc-Gly-S-trans-trans-farnesyl-Cys-OCH$_3$ Yellow oil. Yield 61%, 2.27 g. $^1$H NMR (CDCl$_3$) δ 1.45 (s, 9H), 1.60 (s, 6H), 1.66 (s, 3H), 1.68 (s, 3H), 1.94–2.09 (m, 8H), 2.81 (ABX, J=5.1, 6.2, 13.9 Hz, 2H), 3.16 (m, 2H), 3.76 (s, 3H), 3.85 (t, J=5.5 Hz, 2H), 4.80 (m, 1H), 5.10 (m, 2H), 5.18 (m, 2H), 6.86 (br d, J=7.3 Hz, 1H); MS (MALDI-TOF), 496.5 (M$^+$).

N-Boc-Gly-S-trans-trans-farnesyl Cys-OH (11) Clear oil. Yield 61%, 0.74 g. $^1$H NMR (CDCl$_3$) δ 1.45 (s, 9H), 1.60 (s, 6H), 1.65 (s, 6H), 1.95–2.20 (m, 8H), 280–3.08 (m, 2H), 3.10–3.27 (m, 2H), 3.70–3.90 (m, 2H), 3.95–4.10 (m, 1H), 4.75–4.95 (m, 1H), 5.08 (m, 2H), 5.20 (m, 1H), 5.41 (s, 1H), 7.10 (m, 1H); IR (KBr), 3338, 2979, 2930, 1725, 1660, 1525, 1241, 1172 cm$^{-1}$; MS (MALDI-TOF), 505.3 (M+Na$^+$)

N-Boc-Gly-S-trans-trans-farnesyl-Cys diazomethyl ketone (HI 401) (12) Yellow oil. Yield 53%, 0.21 g. $^1$H NMR (CDCl$_3$) δ 1.46 (s, 9H), 1.60 (s, 6H), 1.67 (s, 6H), 1.97–2.10 (m, 8H), 2.85 (m, 2H), 3.19 (m, 2H), 3.82 (m, 2H), 4.63 (m, 1H), 5.07–5.24 (m, 3H), 5.68 (s, 1H), 6.93 (m, 1H); $^{13}$C NMR (CDCl$_3$) δ 169.3, 140.1, 135.4, 131.4, 130.9, 128.8, 124.2, 123.1, 119.4, 80.6, 68.0, 65.9, 55.2, 54.8, 52.8, 48.3, 44.5, 39.7, 33.0, 31.7, 31.0, 30.2, 29.7, 28.3, 26.7, 26.4, 23.5, 17.7, 16.2, 16.0; IR(KBr), 3318, 3084, 2983, 2916, 2859, 2105, 1669, 1510, 1369 cm$^{-1}$.

N-Boc-Gly-S-trans-trans-farnesyl-Cys chloromethyl ketone (HI 130) (13) Yield 100%, 0.22 g. $^1$H NMR (CDCl$_3$) δ 1.45 (s, 9H), 1.60 (s, 6H), 1.68 (s, 6H), 1.96–2.09 (m, 8H), 2.81–2.97 (m, 2H), 3.10–3.24 (m, 2H), 3.82 (m, 2H), 4.33 (s, 2H), 4.89 (m, 1H), 5.07–5.22 (m, 3H), 6.94 (m, 1H); $^{13}$C NMR (CDCl$_3$), δ 199.7, 169.9, 156.0, 140.4, 135.3, 131.2, 124.2, 123.5, 123.1, 119.2, 111.5, 109.7, 80.5, 60.3, 55.4, 53.1, 51.8, 47.4, 44.2, 41.1, 39.6, 39.6, 31.8, 29.9, 28.2, 26.7, 26.4, 25.7, 21.0, 17.7, 16.1, 16.0, 14.1; IR (KBr), 3309, 2987, 2925, 1695, 1514, 1175 cm$^{-1}$; MS (MALDI-TOF), 379.4 (M−Boc−Cl).

N-Ac-S-methyl-cysteine chloromethyl ketone (4h, 1H 314) Yellow oil. Yield 10%. $^1$H NMR (CDCl$_3$) δ 2.04 (s, 3H), 2.11 (s, 3H), 2.98 (ABX, J=6.0, 6.3, 14.0 Hz, 2H), 4.36 (m, 2H), 4.87 (m, 1H), 6.41 (br d, 1H); $^{13}$C NMR (CDCl$_3$) δ 16.1, 22.9, 35.0, 47.4, 55.0, 170.3, 200.0; GC/MS 209 (M$^+$); IR (KBr) 3278, 2922, 1741, 1659, 1537, 1429, 1209 cm$^{-1}$.

N-Ac-S-ethyl-cysteine chloromethyl ketone (4i, HI 315) Yellow solid. Yield 45%. $^1$H NMR (CDCl$_3$) δ 1.24 (t, J=7.4 Hz, 3H), 2.03 (s, 3H), 2.54 (q, J=7.3 Hz, 2H), 2.93 (ABX, J=6.0, 6.3, 14.0 Hz, 2H), 4.34 (m, 2H), 4.88 (m, 11H), 6.36 (br d, 1H); $^{13}$C NMR (CDCl$_3$) δ 10.0, 18.3, 22.0, 27.9, 42.7, 50.7, 165.5, 195.4; GC/MS 194 (M-CH$_2$CH$_3$); IR (KBr) 3299, 2927, 2872, 1740, 1659, 1537, 1535, 1425, 1371 cm$^{-1}$.

N-Ac-S-propylysteine chloromethyl ketone (4j, HI 369) Yellow semi-solid. Yield 20%. $^1$H NMR (CDCl$_3$) δ 0.96 (t, J=7.3 Hz, 3H), 1.57 (m, 2H), 2.03 (s, 3H), 2.50 (t, J=7.3 Hz, 2H), 2.91 (m, 2H), 4.33 (m, 2H), 4.77 (m, 1H), 6.32 (br d, 1H); $^{13}$C NMR (CDCl$_3$) δ 13.2, 22.6, 22.7, 32.5, 34.5, 47.6, 55.5, 170.6, 200.0; GC/MS 238 (M+1); IR (KBr) 3020, 2976, 2933, 1740, 1676, 1518, 1423, 1215 cm$^{-1}$.

N-Ac-S-butyl-cysteine chloromethyl ketone (4k, HI 363) Yellow solid. Yield 65%. m.p. =75–76° C. $^1$H NMR (CDCl$_3$) δ 0.90 (t, J=7.1 Hz, 3H), 1.38 (m, 2H), 1.52 (m, 2H), 2.04 (s, 3H), 2.53 (t, J=7.3 Hz, 2H), 2.98 (ABX, J=6.0, 6.3, 14.0 Hz, 2H), 4.28 (m, 2H), 4.93, (m, 1H), 6.21 (br d, 1H); $^{13}$C NMR (CDCl$_3$) δ 14.2, 22.9, 31.4, 32.4, 32.9 47.4, 55.4, 170.1, 200.0; GC/MS 215 (M−HCl); MS (MALDI-TOF) 250 (M$^+$); IR (KBr) 3425, 3020, 1732, 1651, 1537, 1466 cm$^{-1}$.

N-Ac-S-pentyl-cysteine chloromethyl ketone (4l, HI 224) Yellow solid. Yield 41% yield. m.p.=74–75° C. $^1$H NMR (CDCl$_3$) δ 0.86 (t, J=6.8 Hz, 3H), 1.2–1.4 (m, 2H), 2.04 (s, 3H), 2.52 (t, J=7.5 Hz, 2H), 2.93 (ABX, J=6.0, 6.3, 13.5 Hz, 2H), 4.32 (m, 2H), 4.89 (m, 1H), 6.26 (br d, 1H); $^{13}$C NMR (CDCl$_3$) δ 14.1, 22.7, 22.9, 28.7, 29.2, 29.6, 31.9, 32.9, 47.4, 55.4, 170.1, 200.0; GC/MS 266 (M+1); MS (MALDI-TOF) 266 (M+1); IR (KBr) 3296, 2918, 2850, 1738, 1660, 1539, 1464 cm$^{-1}$.

N-Ac-S-hexyl-cysteine chloromethyl ketone (4m, HI 357) Yellow solid. Yield 44%. m.p.=75–77° C. $^1$H NMR (CDCl$_3$) δ 0.87 (t, J=6.7 Hz, 3H), 1.2–1.4 (m, 6H), 1.56 (m, 2H), 2.05 (s, 3H), 2.53 (t, J=7.4 Hz, 2H), 2.93 (ABX, J=5.8, 6.0, 13.9 Hz, 2H), 4.35 (m, 2H), 4.89 (m, 1H), 6.36 (br d, 1H); $^{13}$C NMR (CDCl$_3$) δ 14.0, 22.5, 22.9, 28.4, 29.4, 29.6, 31.3, 32.8, 47.4, 55.4, 170.1, 200.0; GC/MS 243 (M−HCl); IR (KBr) 3304, 3053, 2951, 2926, 2870, 1738, 1639, 1537, 1425, 1371, 1283 cm$^{-1}$.

N-Ac-S-heptyl-cysteine chloromethyl ketone (4n, HI 263) Yellow solid. Yield 19%. m.p.=77–81° C. $^1$H NMR (CDCl$_3$) δ 0.87 (t, J=6.6 Hz, 3H), 1.2–1.4 (m, 8H), 1.54 (m, 2H), 2.03 (s, 3H), 2.51 (t, J=7.3 Hz, 2H), 2.92 (ABX, J=5.8, 6.3, 13.7 Hz, 2H), 4.32 (m, 2H), 4.88 (m, 1H), 6.25 (br d, 1H); $^{13}$C NMR (CDCl$_3$) δ 14.1, 22.5, 22.9, 28.6, 28.7, 29.4, 31.6, 32.7, 32.8, 47.4, 55.4, 170.1, 200.0; GC/MS 259 (M+1−Cl); MS (MALDI-TOF) 294 (M+1); IR (KBr) 3306, 2918, 2922, 1737, 1641, 1537, 1466, 1372, 1283, 1134 cm$^{-1}$.

N-Ac-S-octyl-cysteine chloromethyl ketone (4o, HI 352) Yellow solid. Yield 30% yield. m.p.=76–77° C. $^1$H NMR (CDCl$_3$) δ 0.88 (t, J=6.9 Hz, 3H), 1.2–1.4 (m, 10H), 1.55 (m, 2H), 2.05 (s, 3H), 2.53 (t, J=7.4 Hz, 2H), 2.93 (m, 2H), 4.35 (m, 2H), 4.87 (m, 1H), 6.36 (br d, 1H); $^{13}$C NMR (CDCl$_3$) δ 14.0, 22.5, 28.4, 29.3, 31.3, 32.7, 32.9, 47.3, 55.3, 170.0, 199.7; GC/MS 271 N−HCl); IR (KBr) 3300, 3055, 2918, 2852, 1738, 1639, 1537, 1425, 1371, 1283 cm$^{-1}$.

N-Ac-S-nonyl-cysteine chloromethyl ketone (4p, HI 364) Yellow solid. Yield 35%. m.p.=78–81° C. $^1$H NMR (CDCl$_3$) δ 0.86 (t, J=6.5 Hz, 3H), 1.2–1.4 (m, 12H), 1.58 (m, 2H), 2.06 (s, 3H), 2.56 (t,J=7.3 Hz, 2H), 2.98 (ABX, J=6.1, 6.3, 13.8 Hz, 2H), 4.36 (m, 2H), 4.86 (m, 1H), 6.41 (br d, 1H); $^{13}$C NMR (CDCl$_3$) δ 14.1, 22.6, 22.9, 28.7, 29.1, 29.2, 29.4, 31.8, 32.7, 32.8, 47.4, 55.4, 170.2, 200.0; GC/MS 285 (M−HCl); MS (MALDI-TOF) 322 (M+1); IR (KBr) 3302, 2920, 2850, 1738, 1643, 1537, 1394 cm$^{-1}$.

N-Ac-S-decyl-cysteine chloromethyl ketone (4q, HI 371) Yellow solid. Yield 10%. m.p.=80–81° C. $^1$H NMR (CDCl$_3$) δ 0.86 (t, J=6.7 Hz, 3H), 1.2–1.4 (m, 14H), 1.59 (m, 2H), 2.06 (s, 3H), 2.56 (t, J=7.3 Hz, 2H), 2.98 (ABX, J=6.0, 6.3, 13.7 Hz, 2H), 4.28 (m, 2H), 4.93 (m, 1H), 6.21 (br d, 1H); $^{13}$C NMR (CDCl$_3$) δ 14.1, 22.7, 22.9, 28.7, 29.2, 29.3, 29.4, 29.5, 31.9, 32.8, 47.4, 55.4, 170.1, 200.0; MS (ALDI-TOF) 301 (M−Cl); IR (KBr) 3302, 2920, 2850, 1736, 1635, 1539, 1467 cm$^{-1}$.

N-Ac-S-undecyl-cysteine chloromethyl ketone (4r, HI 321) Yellow solid. Yield 25%. m.p.=85–86° C. $^1$H NMR (CDCl$_3$) δ 0.86 (t, J=6.7 Hz, 3H), 1.2–1.4 (m, 16H), 1.59 (m, 2H), 2.06 (s, 3H), 2.56 (t, J=7.3 Hz, 2H), 2.98 (ABX, J=6.0, 6.3, 13.7 Hz, 2H), 4.28 (m, 2H), 4.93 (m, 1H), 6.21 (br d, 1H); $^{13}$C NMR (CDCl$_3$) δ 14.1, 22.7, 22.9, 28.7, 29.2, 29.3, 29.4, 29.5, 29.6, 31.9, 32.8, 32.9, 47.4, 55.4, 170.1, 200.0; GC/MS 313 (M−Cl); MS (MALDI-TOF) 313 (M−Cl); IR (KBr) 3305, 2918, 2850, 1738, 1651, 1537, 1466 cm$^{-1}$.

N-Ac-S-tridecyl-cysteine chloromethyl ketone (4s, 1H 323) Yellow solid. Yield 22%. m.p.=83–84° C. $^1$H NMR (CDCl$_3$) δ 0.87 (t, J=6.3 Hz, 3H), 1.2–1.4 (m, 20H), 1.59 (m, 2H), 2.06 (s, 31), 2.56 (t, J=7.2 Hz, 2H), 2.98 (ABX, J=5.8, 6.0, 14.0 Hz, 2H), 4.28 (m, 2H), 4.93 (m, 1H), 6.21 (br d, 1H); $^{13}$C NMR (CDCl$_3$) δ 14.1, 22.7, 23.0, 28.8, 29.2, 29.4, 29.4, 29.5, 29.6, 31.9, 32.8, 32.9, 47.3, 55.4, 170.1, 200.0; GC/MS 341 (M−HCl); MS (MALDI-TOF) 379 (M+2); IR (KBr) 3307, 2916, 2850, 1737, 1651, 1537, 1466, 1402, 1282 cm$^{-1}$.

N-Ac-S-tetradecyl-cysteine chloromethyl ketone (4t, HI 354) Yellow solid. Yield 32%. m.p.=79–80° C. $^1$H NMR (CDCl$_3$) δ 0.88 (t, J=6.7 Hz, 3H), 1.2–1.4 (m, 22H), 1.57 (m, 2H), 2.06 (s, 3H), 2.51 (t, J=7.3 Hz, 2H), 2.94 (ABX, J=6.0, 6.3, 13.9 Hz, 2H), 4.35 (m, 2H), 4.90 (m, 1H), 6.30 (br d, 1H); $^{13}$C NMR (CDCl$_3$) δ 14.1, 22.7, 22.9, 28.7, 29.2, 29.35, 29.4, 29.6, 29.7, 31.9, 32.8, 32.9, 47.3, 55.4, 170.1, 200.0;

GC/MS 355 (M−HCl); IR (KBr) 3302, 3259, 2916, 2848, 1738, 1660, 1537, 1464, 1373, 1317cm$^{-1}$.

N-Ac-S-pentadecyl-cysteine chloromethyl ketone (4u, HI 225) Yellow solid. Yield 25%. m.p.=86–89° C. $^1$H NMR (CDCl$_3$) δ 0.86 (t, J=6.5 Hz, 3H), 1.2–1.4 (m, 24H), 1.55 (m, 2H), 2.03 (s, 3H), 2.51 (t, J=6.2 Hz, 2H), 2.91 (ABX, J=6.0, 6.3, 14.0 Hz, 2H), 4.88 (m, 1H), 6.33 (br d, 1H); $^{13}$C NMR (CDCl$_3$) δ 14.1, 22.7, 23.0, 28.8, 29.0, 29.2, 29.4, 29.5, 29.7, 30.7, 31.9, 32.2, 32.8, 32.9, 47.3, 55.4, 170.1, 200.0; GC/MS 369 (M−HCl); MS (MALDI-TOF) 407 (M+2); IR (KBr) 3307, 3124, 2916, 2850, 1738, 1651, 1533, 1487, 1404, 1284 cm$^{-1}$.

N-Ac-S-hexadecylcysteine chloromethyl ketone (4v, HI 366) Yellow solid. Yield 18%. m.p.=87–88° C. $^1$H NMR (CDCl$_3$) δ 0.86 (t, J=6.7 Hz, 3H), 1.2–1.4 (m, 26H), 1.55 (m, 2H), 2.03 (s, 3H), 2.51 (t, J=7.3 Hz, 2H), 2.98 (ABX, J=5.8, 6.0, 14.0 Hz, 2H), 4.32 (m, 2H), 4.93 (m, 1H), 6.26 (br d, 1H); $^{13}$C NMR (CDCl$_3$) δ 14.2, 22.7, 23.0, 28.8, 29.0, 29.2, 29.4, 29.5, 29.7, 31.9, 32.8, 32.9, 47.3, 55.4, 170.1, 200.0; GC/MS 383 (M−Cl); MS (MALDI-TOF) 382 (M−HCl); IR (KBr) 3259, 2916, 2848, 1740, 1660, 1539, 1471, 1432, 1134 cm$^{-1}$.

N-Ac-S-octadecylcysteine chloromethyl ketone (4w, HI 370) Yellow solid. Yield 78%. m.p.=84–86° C. $^1$H NMR (CDCl$_3$) δ 0.88 (t, J=6.7 Hz, 3H), 1.2–1.4 (m, 30H), 1.57 (m, 2H), 2.06 (s, 3H), 2.53 (t, J=7.4 Hz, 2H), 2.94 (ABX, J=5.8, 6.3, 13.7 Hz, 2H), 4.35 (m, 2H), 4.90 (m, 1H), 6.31 (br d, 1H); $^{13}$C NMR (CDCl$_3$) δ 14.2, 22.7, 23.0, 28.9, 29.2, 29.35, 29.4, 29.5, 29.6, 29.7, 31.9, 32.8, 32.9, 34.4, 47.3, 55.4, 170.0, 200.0; IR (KBr) 3313, 2916, 2850, 1738, 1651, 1537, 1466, 1385, 1281, 1254 cm$^{-1}$.

N-Ac-S-eicoyl-cysteine chloromethyl ketone (4x, HI 226) Yellow solid. Yield 11%. m.p.=84–89° C. $^1$H NMR (CDCl$_3$) δ 0.87 (t, J=6.6 Hz, 3H), 1.2–1.4 (m, 34H), 1.55 (m, 2H), 2.04 (s, 3H), 2.52 (t, J=7.9 Hz, 2H), 2.92 (ABX, J=6.0, 7.7, 14.0 Hz, 2H), 4.32 (m, 2H), 4.92 (m, 1H), 6.28 (br d, 1H); $^{13}$C NMR (CDCl$_3$) δ 14.2, 22.7, 23.0, 28.7, 29.2, 29.4, 29.5, 29.6, 29.7, 31.9, 32.8, 32.9, 47.3, 55.4, 170.0, 200.0; MS (MALDI-TOF) 477 (M+2); IR (KBr) 3307, 2918, 2850, 1736, 1662, 1541, 1464, 1261, 1097cm$^{-1}$.

N-Ac-S-docosyl-cysteine chloromethyl ketone (4y, HI 322) Yellow solid. Yield 15%. m.p.=95–97° C. $^1$H NMR (CDCl$_3$) δ 0.88 (t, J=6.5 Hz, 3H), 1.2–1.4 (m, 38H), 1.55 (m, 2H), 2.04 (s, 3H), 2.52 (t, J=7.8 Hz, 2H), 2.92 (ABX, J=6.0, 6.3, 14.0 Hz, 2H), 4.32 (m, 2H), 4.92 (m, 1H), 6.28 (br d, 1H); $^{13}$C NMR (CDCl$_3$) δ 14.2, 22.7, 23.0, 28.8, 29.2, 29.4, 29.5, 29.7, 31.9, 32.8, 32.9, 47.3, 55.4, 170.1, 200.0; MS (MALDI-TOF) 493 (M+2−Cl+Na); IR (KBr) 3259, 2918, 2848, 1740, 1660, 1537, 1471, 1261, 1099 cm$^{-1}$.

N-Ac-S-allyl-cysteine chloromethyl ketone (11–419) Pale yellow solid: $^1$H NMR (CDCl$_3$) δ 2.02 (s, 3H), 2.85 (m, 2H), 3.12 (d, 2H), 4.31 (m, 2H), 4.87 (m, 1H), 5.12 (dd, 1H), 5.16 (s, 1H), 5.74 (m, 1H), 6.32 (br, 1H).

N-Ac-S-t-butyl-cysteine chloromethyl ketone (HI-349) Pale yellow solid: $^1$H NMR (CDCl$_3$) δ 1.24 (s, 9H), 1.97 (s, 3H), 2.90 (dd, 2H), 4.27 (m, 2H), 4.87 (m, 1H), 6.32 (br, 1H); MS (EI) m/z 251 (M$^+$).

N-Ac-S-2-methylpropyl-cysteine chloromethyl ketone (HI-391) Pale yellow solid: $^1$H NMR (CDCl$_3$) δ 0.94 (m, 6H), 1.74 (m, 1H), 2.01 (s, 3H), 2.40 (d, 2H), 2.87 (t, 2H), 4.33 (m, 2H), 4.83 (m, 1H), 6.51 (d, 1H); MS (EI) m/z 252 (M$^+$).

N-Ac-S-2,2-dimethylpropylcysteine chloromethyl ketone (HI-421) Pale yellow solid: $^1$H NMR (CDCl$_3$) δ 1.32 (s, 9H), 2.06 (s, 3H), 3.15 (m, 2H), 3.45 (m, 2H), 4.34 (s, 2H), 4.94 (m, 1H), 6.42 (d, 1H); MS (EI) m/z 227 (M−$^t$Bu).

N-Ac-S-3-methylbutyl-cysteine chloromethyl ketone (HI-387) Pale yellow solid: $^1$H NMR (CDCl$_3$) δ 0.89 (d, 6l), 1.44 (m, 1H), 1.62 (m, 2H), 2.04 (s, 3H), 2.53 (t, 2H), 2.93 (m, 2H), 4.34 (m, 2H), 4.88 (m, 1H), 6.30 (d, 1H); MS (EI) m/z 229 (M−Cl).

N-Ac-S-2-ethylbutyl-cysteine chloromethyl ketone (HI-390) Pale yellow solid: $^1$H NMR (CDCl$_3$) δ 0.83 (m, 6H), 1.35 (m, 5H), 2.03 (s, 3H), 2.51 (d, 2H), 2.90 (m, 2H), 4.32 (d, 2H), 4.87 (m, 1H), 6.34 (d, 1H); MS (EI) m/z 243 (M−Cl).

N-Ac-S-cyclopropylmethylcysteine chloromethyl ketone (HI-507) Pale yellow solid: $^1$H NMR (CDCl$_3$) δ 0.57 (d, 4H), 0.95 (m, 1H), 2.03 (s, 3H), 2.45 (d, 2H), 2.97 (m, 2H), 4.33 (d, 2H), 4.89 (m, 1H), 6.34 (d, 1H).

N-Ac-S-cyclobutylmethylcysteine chloromethyl ketone (HI-385) Pale yellow solid: $^1$H NMR (CDCl$_3$) δ 1.83 (m, 7H), 2.02 (s, 3H), 2.58 (d, 2H), 2.89 (m, 2H), 4.32 (d, 2H), 4.84 (m, 1H), 6.32 (d, 1H); MS (EI) m/z 227 (M−Cl).

N-Ac-S-cyclohexylmethyl-cysteine chloromethyl ketone (HI-386) Pale yellow solid: $^1$H NMR (CDCl$_3$) δ 0.90 (m, 2H), 1.25 (m, 4H), 1.41 (m, 4H), 1.70 (m, 1H), 2.04 (s, 3H), 2.40 (d, 2H), 2.89 (m, 2H), 4.34 (m, 2H), 4.86 (m, 1H), 6.35 (d, 1H).

N-Ac-S-benzylcysteine chloromethyl ketone (HI-251) Pale yellow solid: $^1$H NMR (CDCl$_3$) δ 1.98 (s, 3H), 2.82 (m, 2H), 3.70 (s, 2H), 4.08 (d, 2H), 4.82 (m, 1H), 6.18 (d, 1H), 7.29 (m, 5H).

N-Ac-S-4-methoxybenzyl-cysteine chloromethyl ketone (HI-349) Pale yellow solid: $^1$H NMR (CDCl$_3$) δ 1.91 (s, 3H), 2.78 (m, 2H), 3.62 (s, 3H), 3.73 (s, 2H), 4.12 (d, 2H), 4.74 (m, 1H), 6.07 (d, 1H), 6.80 (m, 2H), 7.18 (m, 2H); MS (EI) m/z 279 (M−Cl).

N-Ac-S-benzyloxycarbonyl-cysteine chloromethyl ketone (HI-389) Pale yellow solid: $^1$H NMR (CDCl$_3$) δ 1.98 (s, 3H), 3.36 (m, 2H), 4.31 (d, 2H), 5.01 (m, 2H), 5.42 (m, 1H), 6.43 (d, 1H), 7.35 (m, 5H).

N-Ac-S-diphenylmethyl-cysteine chloromethyl ketone (HI-418) Pale yellow solid: $^1$H NMR (CDCl$_3$) δ 2.00 (m, 4H), 3.37 (m, 2H), 4.34 (d, 2H), 5.02 (m, 1H), 6.53 (d, 1H), 7.30 (m, 10H).

N-Ac-S-trityl-cysteine chloromethyl ketone (HI-350) Pale yellow solid: $^1$H NMR (CDCl$_3$) δ 1.92 (s, 3H), 2.73 (m, 2H), 3.89 (s, 2H), 4.40 (m, 1H), 5.82 (d, 1H), 7.21 (m, 15H).

N-Ac-S-2-naphthylmethyl-cysteine chloromethyl ketone (HI-392) Pale yellow solid: $^1$H NMR (CDCl$_3$) δ 1.89 (s, 3H), 2.81 (m, 2H), 3.84 (s, 2H), 4.13 (d, 2H), 4.83 (m, 1H), 6.10 (d, 1H), 7.43 (m, 2H), 7.66 (s, 1H), 7.72 (m, 4H).

N-Ac-O-dodecyl-serine chloromethyl ketone (HI-489) White solid: $^1$H NMR (CDCl$_3$) δ 0.88 (t, 3H), 1.26 (m, 20H), 2.05 (s, 3H), 3.41 (t, 2H), 3.57 (m, 1H), 3.88 (m, 1H), 4.29 (d, 2H), 4.90 (m, 1H), 6.32 (d, 1H).

N-Boc-O-dodecyl serine chloromethyl ketone (HI-266) Pale yellow solid: $^1$H NMR (CDCl$_3$) δ 0.88 (t, 3H), 1.26 (m, 20H), 1.46 (s, 9H), 3.41 (t, 2H), 3.50 (m, 1H), 3.57 (dd, 1H), 4.37 (d, 2H), 4.56 (m, 1H), 5.21 (d, 1H); MS (EI) m/z 357 (M−Cl).

N-Propyloxycarbonyl-S-dodecylcysteine chloromethyl ketone (HI-413) Pale yellow solid: $^1$H NMR (CDCl$_3$) δ 0.92 (m, 6H), 1.25 (m, 20H), 1.60 (m, 2H), 2.52 (t, 2H), 2.91 (d, 2H), 4.01 (t, 2H), 4.45 (s, 2H), 4.66 (m, 1H), 5.48 (d, 1H); MS (EI) m/z 371 (M−Cl).

N-Benzyloxycarbonyl-S-dodecylcysteine chloromethyl ketone (HI-320) Pale yellow solid: $^1$H NMR (CDCl$_3$) δ 0.86 (t, 3H), 1.27 (m, 20H), 2.49 (t, 2H), 2.91 (d, 2H), 4.32 (s, 2H), 4.70 (m, 1H), 5.19 (s, 2H), 5.59 (d, 1H), 7.32 (s, 5H); MS (EI) m/z 419 (M−Cl).

N-9Fluorenylmethyloxycarbonyl-S-dodecyl-cysteine chloromethyl ketone (HI-398) Pale yellow solid: $^1$H NMR (CDCl$_3$) δ 0.87 (t, 3H), 1.24 (m, 18H), 1.52 (m, 2H), 2.52 (t, 2H), 2.93 (m, 2H), 4.22 (t, 1H), 4.28 (s, 2H), 4.46 (m, 2H), 4.68 (m, 1H), 5.59 (d, 1H), 7.35–7.77 (m, 8H).

N-3-Dimethylaminobenzoyl-S-dodecyl-cysteine chloromethyl ketone (HI-268) Pale yellow solid: $^1$H NMR (CDCl$_3$) δ 0.94 (t, 3H), 1.26 (m, 20H), 2.54 (t, 2H), 3.01 (d, 2H), 3.93 (d, 6H), 4.13 (d, 2H), 4.68 (m, 1H), 5.53 (d, 1H), 7.00 (dd, 1H), 7.40 (m, 3H).

N-Ac-S-dodecyl-cysteine bromomethyl ketone (HI-488) Pale yellow solid: $^1$H NMR (CDCl$_3$) δ 0.84 (t, 3H), 1.22 (m, 18H), 1.53 (m, 2H), 2.02 (s, 3H), 2.50 (t, 2H), 2.92 (m, 2H), 4.12 (s, 2), 4.89 (m, 1H), 6.44 (d, 1H).

N-Ac-S-dodecyl-Cys-N(OCH$_3$)-CH$_3$ (HI-267) Pale yellow oil: $^1$H NMR (CDCl$_3$) δ 0.87 (t, 3H), 1.25 (m, 20H), 2.02 (s, 3H), 2.51 (t, 2H), 2.82 (m, 2H), 3.22 (s, 3H), 3.79 (s, 3H), 5.17 (m, 1H), 6.38 (d, 1H); MS (EI) m/z 314 (M–N(OCH$_3$)CH$_3$).

N-Ac-S-dodecyl-Cys-H (HI-274) White solid: $^1$H NMR (CDCl$_3$) δ 0.88 (t, 3H), 1.26 (m, 18H), 1.58 (m, 2H), 2.09 (s, 3H), 2.54 (t, 2H), 3.00 (m, 2H), 4.63 (m, 1H), 6.37 (d, 1H), 9.65 (s, 1H).

N-Ac-S-dodecyl-Cys-CH$_2$-SPh (HI-269) Pale yellow solid: $^1$H NMR (CDCl$_3$) δ 0.88 (t, 3H), 1.25 (m, 18H), 1.53 (m, 2H), 1.97 (s, 3H), 2.46 (t, 2H), 2.2 (m, 2H), 5.16 (m, 1H), 5.43 (s, 2H), 6.16 (d, 1H), 7.33 (s, 5H).

N-Ac-S-dodecyl-Cys-CH$_2$-S-2-naphthyl (HI-302) Pale yellow solid: $^1$H NMR (CDCl$_3$) δ 0.81 (t, 3H), 1.16 (m, 18H), 1.39 (m, 2H), 1.84 (s, 3H), 2.36 (t, 2H), 2.77 (m, 2H), 5.18 (m, 1H), 5.59 (s, 2H), 6.08 (d, 1H), 7.43 (s, 3H), 7.73 (m, 4H).

N-Ac-S-dodecyl-Cys-CH$_2$-S-CH$_2$CH$_2$CO$_2$H (HI-273) White solid: $^1$H NMR (CDCl$_3$) δ 0.88 (t, 3H), 1.26 (m, 18H), 1.33 (m, 2H), 2.07 (s, 3H), 2.54 (t, 2H), 2.77 (m, 4H), 2.97 (m, 2H), 3.48 (m, 2H), 5.02 (m, 1H), 6.44 (d, 1H), 8.04 (br, 1H).

EXAMPLE 3

Cytotoxicity of all ketone compounds

The cytotoxicity of the alkyl ketone compounds against tumor cells was evaluated in leukemic cells, breast cancer cells, prostate cancer cells, and brain cancer cells.

Cytotoxicity Assay

Cytotoxicity of various compounds against tumor cells was performed using the MTT (3-[4,5-methylthiazol-2-yl]-2,5-diphenyl tetrazolium bromide) assay (Boehringer Mannheim Corp., Indianapolis, Ind.). Unless otherwise specified, all cell lines were obtained from the American Type Culture Collection (ATCC). Briefly, exponentially growing cells were seeded into a 96-well plate at a density of 2.5×10$^4$ cells/well and incubated for 36 hours at 37° C. prior to drug exposure. On the day of treatment, culture medium was carefully aspirated from the wells and replaced with fresh medium containing the indicated compound at concentrations ranging from 0.1 to 250 μM. Triplicate wells were used for each treatment.

Human leukemic cell lines (NALM-6, MOLT-3) glioblastoma cells (U373) and human breast tumor cell lines (BT20 and MDA-MB-231) were obtained from the American Type Culture Collection and maintained as a continuous cell line in Dulbecco's modified Eagles's medium supplemented with 10% fetal bovine serum and antibiotics.

The cells were incubated with the various compounds for 24–36 hours at 37° C. in a humidified 5% CO$_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 um. To translate the OD$_{540}$ values into the number of live cells in each well, the OD$_{540}$ values were compared to those on standard OD$_{540}$—versus—cell number curves generated for each cell line. The percent survival was calculated using the formula:

$$\% \text{ Survival} = \frac{\text{live cell number [test]}}{\text{live cell number [control]}} \times 100$$

The IC$_{50}$ values were calculated by non-linear regression analysis and are shown below in Tables 1–6.

TABLE 1

Structure and activities of S-alkyl cysteine diazo and chloromethyl ketone derivatives against Nalm-6 (B-lineage ALL), Molt-3 (T-lineage ALL), BT-20 (breast cancer), PC-3 (prostate cancer) and U-373 (glioblastoma) cell lines.

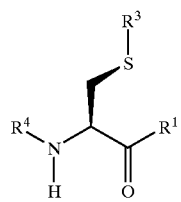

| No. | HI No. | R$^4$ | R$^3$ | R$^1$ | Nalm-6 B-lineage ALL | Molt-3 T-lineage ALL | BT-20 Breast Cancer | PC-3 Prostate Cancer | U-373 Glioblastoma |
|---|---|---|---|---|---|---|---|---|---|
| 12 | 401 | Boc—Gly | trans,trans-Farnesyl | CH=N$_2$ | 51.3 | 84.5 | 95.1 | 90.6 | >100 |
| 3b | 82 | Boc | trans,trans-Farnesyl | CH=N$_2$ | 49.8 | 50.1 | >100 | >100 | >100 |
| 3a | 367 | Ac | trans,trans-Farnesyl | CH=N$_2$ | 30.3 | 32.2 | >100 | >100 | >100 |
| 3c | 122 | Ac | trans-Geranyl | CH=N$_2$ | >100 | >100 | >100 | >100 | >100 |
| 3d | 123 | Ac | 3-Methyl-2-butenyl | CH=N$_2$ | >100 | >100 | >100 | >100 | >100 |
| 3e | 348 | Ac | Dodecyl | CH=N$_2$ | 15.4 | 22.9 | 97.9 | >100 | >100 |
| 13 | 130 | Boc—Gly | trans,trans-Farnesyl | CH$_2$—Cl | 12.9 | 17.5 | >100 | >100 | 71.3 |

TABLE 1-continued

Structure and activities of S-alkyl cysteine diazo and chloromethyl ketone
derivatives against Nalm-6 (B-lineage ALL), Molt-3 (T-lineage ALL), BT-20
(breast cancer), PC-3 (prostate cancer) and U-373 (glioblastoma) cell lines.

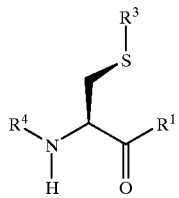

| No. | HI No. | $R^4$ | $R^3$ | $R^1$ | Nalm-6 B-lineage ALL | Molt-3 T-lineage ALL | BT-20 Breast Cancer | PC-3 Prostate Cancer | U-373 Glioblastoma |
|---|---|---|---|---|---|---|---|---|---|
| | | | | | \multicolumn{5}{c}{$IC_{50}$ ($\mu$M)} |
| 4b | 124 | Boc | trans,trans-Farnesyl | $CH_2$—Cl | 10.7 | 7.7 | >100 | >100 | >100 |
| 4a | 368 | Ac | trans,trans-Farnesyl | $CH_2$—Cl | 3.0 | 1.4 | 55.8 | 26.8 | 61.3 |
| 4c | 127 | Ac | trans-Geranyl | $CH_2$—Cl | >100 | >100 | >100 | >100 | >100 |
| 4d | 128 | Ac | 3-Methyl-2-butenyl | $CH_2$—Cl | 12.6 | 7.9 | 25.7 | 47.8 | >100 |
| 4e | 131 | Ac | Dodecyl | $CH_2$—Cl | 2.0 | 10.9 | 10.0 | 22.1 | 35.1 |
| 8 | 129 | Boc | Dodecyl | $CH_2$—Cl | 15.1 | 15.5 | 48.9 | 64.6 | >100 |
| 9 | 252 | H.HCl | Dodecyl | $CH_2$—Cl | 17.7 | 12.5 | >100 | >100 | >100 |

TABLE 2

Structure and activities of farnesylthio methyl ketone derivatives against
Nalm-6 (B-lineage ALL), Molt-3 (T-lineage ALL), BT-20 (breast cancer),
PC-3 (prostate cancer) and U-373 (glioblastoma) cell lines.

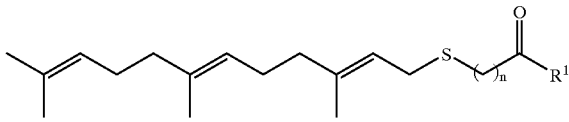

| No. | HI Number | n | $R^1$ | Nalm-6 B-lineage ALL | Molt-3 T-lineage ALL | BT-20 Breast Cancer | PC-3 Prostate Cancer | U-373 Glioblastoma |
|---|---|---|---|---|---|---|---|---|
| | | | | \multicolumn{5}{c}{$IC_{50}$ ($\mu$M)} |
| 3f | 84 | 1 | CH=$N_2$ | >100 | 60.3 | >100 | >100 | >100 |
| 3g | 83 | 2 | CH=$N_2$ | 53.5 | 6.8 | >100 | >100 | >100 |
| 4f | 126 | 1 | $CH_2$—Cl | 84.3 | >100 | >100 | >100 | >100 |
| 4g | 125 | 2 | $CH_2$—Cl | 40.7 | 35.5 | >100 | >100 | >100 |

TABLE 3

Comparison of the effect of the S-alkyl chain length upon the activities of cysteine chloromethyl ketone derivatives against Nalm-6 (B-lineage ALL) and Molt-3 (T-lineage ALL), BT-20 (breast cancer), PC-3 (prostate cancer) and U-373 (glioblastoma) cell lines

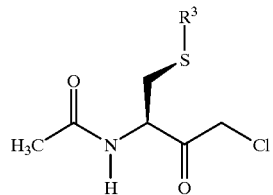

| No. | HI No. | $R^3$ | Nalm-6 B-lineage ALL | Molt-3 T-lineage ALL | BT-20 Breast Cancer | PC-3 Prostate Cancer | U-373 Glioblastoma |
|---|---|---|---|---|---|---|---|
| | | | IC$_{50}$ ($\mu$M) | | | | |
| 4h | 314 | Methyl | 30.3 | 80.8 | >100 | >100 | >100 |
| 4I | 315 | Ethyl | 52.8 | 99.9 | 96.4 | 41.2 | >100 |
| 4j | 369 | Propyl | 6.9 | 8.0 | >100 | 37.7 | 97.7 |
| 4k | 363 | Butyl | 41.4 | 5.6 | >100 | >100 | 86.9 |
| 4l | 224 | Pentyl | 5.8 | 5.4 | 89.5 | >100 | >100 |
| 4m | 357 | Hexyl | 3.3 | 0.7 | >100 | 25.1 | 91.9 |
| 4n | 263 | Heptyl | 4.8 | 2.5 | 84.9 | 31.3 | 62.6 |
| 4o | 352 | Octyl | 5.6 | 4.1 | 58.8 | 35.4 | >100 |
| 4p | 364 | Nonyl | 7.3 | 6.7 | >100 | 96.3 | 88.2 |
| 4q | 371 | Decyl | 4.7 | 3.4 | >100 | >100 | 86.2 |
| 4r | 321 | Undecyl | 1.7 | 3.0 | 99.1 | 64.7 | 56.7 |
| 4e | 131 | Dodecyl | 2.0 | 10.9 | 10.0 | 22.1 | 35.1 |
| 4s | 323 | Tridecyl | >100 | >100 | >100 | >100 | >100 |
| 4t | 354 | Tetradecyl | 8.7 | 8.8 | >100 | 54.8 | >100 |
| 4u | 225 | Pentadecyl | 8.9 | 8.6 | >100 | >100 | >100 |
| 4v | 366 | Hexadecyl | 16.0 | 17.3 | >100 | >100 | >100 |
| 4w | 370 | Octadecyl | >100 | >100 | >100 | >100 | >100 |
| 4x | 226 | Eicosyl | >100 | >100 | >100 | >100 | >100 |
| 4y | 322 | Docosyl | >100 | >100 | >100 | >100 | >100 |

TABLE 4

Examination of the effect of changing R1 of the molecule.

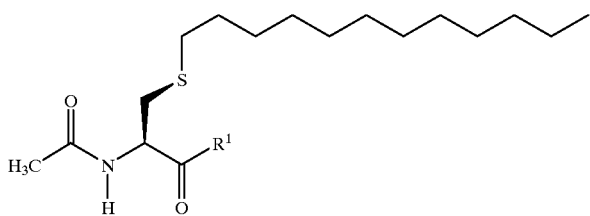

| HI No. | $R^1$ | Nalm-6 | Molt-3 | BT-20 | PC-3 | U373 |
|---|---|---|---|---|---|---|
| | | IC$_{50}$ ($\mu$M) | | | | |
| 131 | CH$_2$—Cl | 2.0 | 2.3 | 10.0 | 22.1 | 35.1 |
| 348 | CH=N$_2$ | 15.4 | 22.9 | 97.9 | >100 | >100 |
| 488 | CH$_2$—Br | 1.3 | 3.19 | 33.83 | 39.6 | 22.5 |
| 208 | OH | | | | | |
| 508 | CH$_2$—O—CO—Ph | | | | | |
| 267 | N(OCH$_3$)CH$_3$ | 50.1 | | >100 | >100 | >100 |
| 274 | H | 12.6 | 13.1 | 22.8 | | >100 |
| 269 | CH$_2$—S—Ph | >100 | >100 | >100 | >100 | >100 |
| 302 | CH$_2$—S-2-naphthyl | >100 | >100 | >100 | >100 | >100 |
| 399 | CH$_2$—S—C$_6$F$_5$ | 91.2 | 40.8 | >100 | 91.6 | >100 |
| 365 | CH$_2$—S-trityl | 93.1 | 97.3 | >100 | >100 | >100 |
| 273 | CH$_2$—S—CH$_2$CH$_2$—CO$_2$H | 44.4 | 50.3 | 20.06 | >100 | >100 |

TABLE 5

Examination of the effect of changing X from S to O and altering R4.

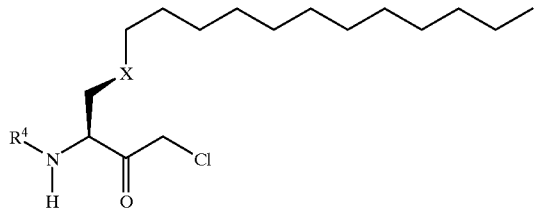

| HI No. | R⁴ | X | IC₅₀ (μM) | | | | |
|---|---|---|---|---|---|---|---|
| | | | Nalm-6 | Molt-3 | BT-20 | PC-3 | U373 |
| 252 | H.HCl | S | 17.7 | 12.5 | >100 | >100 | >100 |
| 131 | Acetyl | S | 2.0 | 2.3 | 10.0 | 22.1 | 35.1 |
| 489 | Acetyl | O | 3.8 | 15.3 | >100 | >100 | >100 |
| 490 | Trifluoroacetyl | S | 32.6 | 41.3 | >100 | >100 | >100 |
| 129 | t-Butyloxycarbonyl | S | 15.1 | 15.5 | 48.9 | 64.6 | >100 |
| 266 | t-Butyloxycarbonyl | O | 64.5 | | 49.9 | | 37.1 |
| 319 | Ethyloxycarbonyl | S | 77.6 | 84.2 | >100 | >100 | >100 |
| 413 | Propyloxycarbonyl | S | | | | | |
| 320 | Benzyloxycarbonyl | S | 13.5 | >100 | >100 | >100 | >100 |
| 398 | 9-Fluorenylmethyloxycarbonyl | S | 25.7 | 32.3 | >100 | >100 | >100 |
| 491 | Benzoyl | S | 5.4 | 6.5 | >100 | 52.1 | >100 |
| 268 | 3-Dimethylaminobenzoyl | S | 96.1 | | >100 | >100 | >100 |

TABLE 6

An examination of the effects of incorporating rings and branched chains into R3.

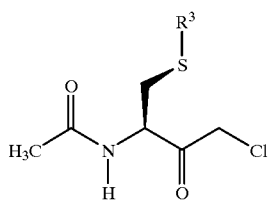

| HI No. | R³ | IC₅₀ (μM) | | | | |
|---|---|---|---|---|---|---|
| | | Nalm-6 | Molt-3 | BT-20 | PC-3 | U373 |
| 419 | Allyl | 4.3 | 7.3 | 55.7 | >100 | 56.7 |
| 400 | 5-Hexenyl | | | | | |
| 349 | t-Butyl | 71.0 | 71.9 | >100 | >100 | >100 |
| 391 | 2-Methylpropyl | | | | | |
| 421 | 2,2-Dimethylpropyl | | | | | |
| 388 | t-Butylthio | | | | | |
| 387 | 3-Methylbutyl | | | | | |
| 390 | 2-Ethylbutyl | | | | | |
| 507 | Cyclopropylmethyl | | | | | |
| 385 | Cyclobutylmethyl | | | | | |
| 386 | Cyclohexylmethyl | | | | | |
| 251 | Benzyl | | | | | |
| 351 | 4-Methoxybenzyl | 60.17 | 4.75 | 73.1 | 43.8 | 45.6 |
| 389 | Benzyloxycarbonyl | 1.2 | 3.5 | 49.3 | 23.4 | 54.4 |
| 418 | Diphenylmethyl | | | | | |
| 350 | Trityl | 10.0 | 26.4 | 88.8 | 52.2 | 87.1 |
| 392 | 2-Naphthylmethyl | 2.6 | 2.9 | 40.4 | 36.6 | 41.8 |
| 420 | 2-Anthraquinonyl-methyl | | | | | |

The data shown in Table I suggest that substitution at the R1 position with a chloromethyl group is better than substitution with a diazomethyl group. Placement of the dodecyl and farnesyl groups at the R3 position produced compounds having the greatest cytotoxicity.

The effect changing the length of R² are reported in Table 2. Omission of the sidegroup caused the cytotoxicity of the compounds to decrease. Additionally, compounds where R² comprises two carbon atoms were more cytotoxic than compounds A series of compounds was prepared with different aliphatic chain lengths in the R³ position to determine the effect of chain length on cytotoxicity. As shown in Table 3, compounds with chain lengths of about 5 to 15 were the most effective anti-cancer agents. Preferred lengths were chain lengths of about 11 to 12.

Various groups were tested in the R¹ position to further define effective anti-cancer compounds. The results are reported in Table 4. Substitution of a bromomethyl group at the R¹ position produced the most effective compound, consistent with Table I where chloromethyl was the most effective compound.

The effect of changing of X and R⁴ on cytotoxicity was examined and reported in Table 5. The data show that a small acetyl substituent as R⁴ produces a potent cytotoxicagent, as both absence of acetyl and substitution with a larger group caused a loss in potency. Substitution of R⁴ with benzoyl produced an effective compound. The effect of changing X to O is more complex, with the derivatives being comparable in some cell lines but different in others. The ether compounds may offer advantages in terms of stability, despite their lower cytotoxic potency.

Various substitutions of R³ were analyzed to determine the effects of branched and ring structures on cytotoxicity. The results demonstrate that ringed and branched structures are effective anti-cancer compounds.

EXAMPLE 4

Cytotoxicity of HI-131 in Primary Cancer Cells

Figure 1B:
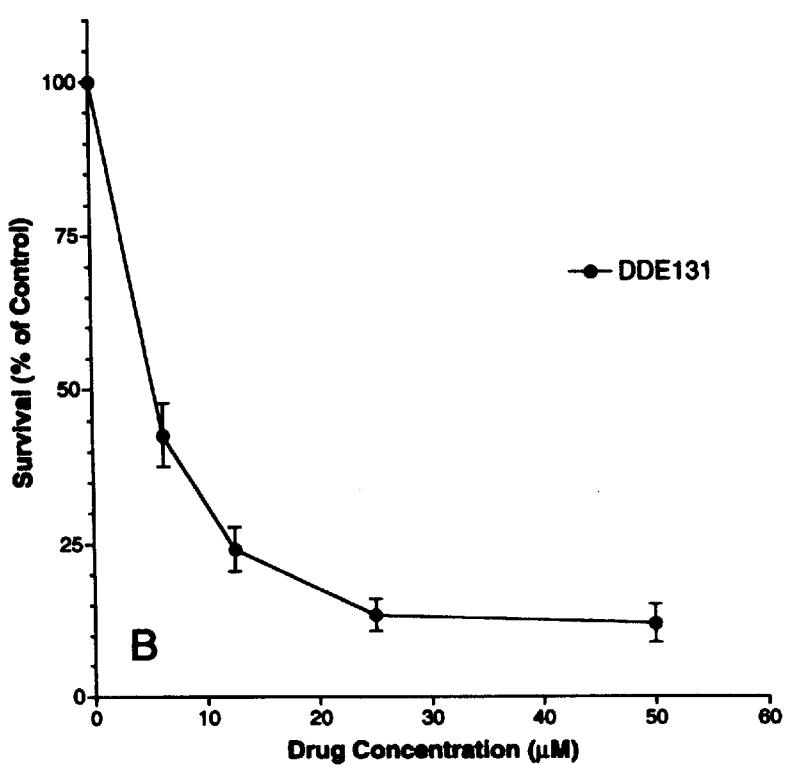
FIG. 1B is a graph showing mean survival as a function of drug concentration from the data of FIG. 1A.
Figure 2A:
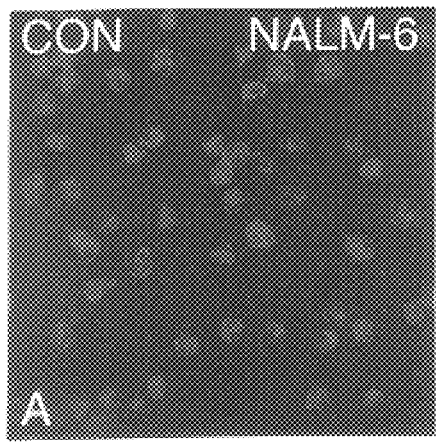
FIGS. 2A–2F show photographs of apoptosis induced by HI-131 in treated human Leukemia cells.
Figure 2B:
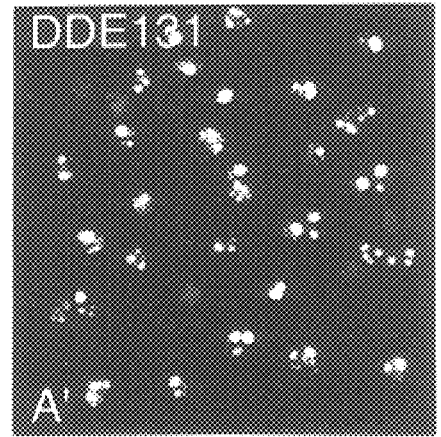
Figure 2C:
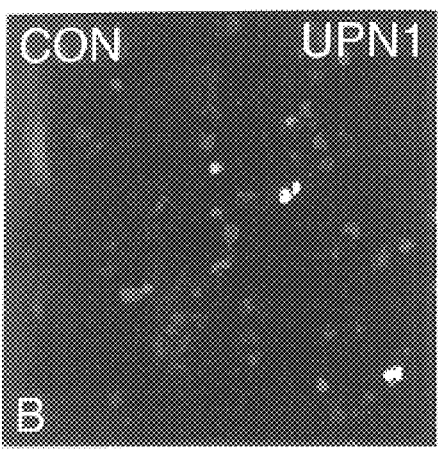
Figure 2D:
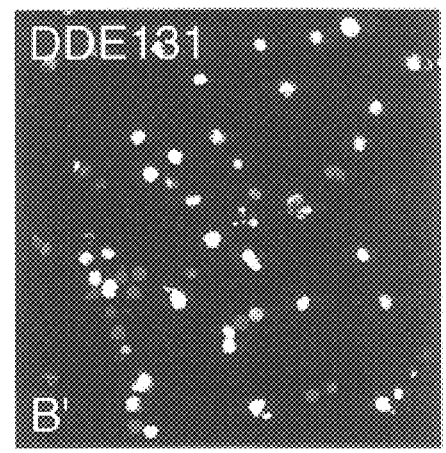
Figure 2E:
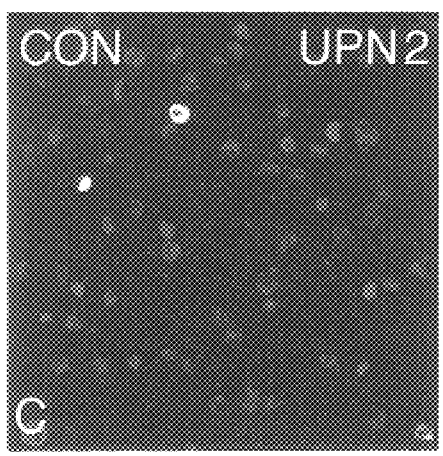
Figure 2F:
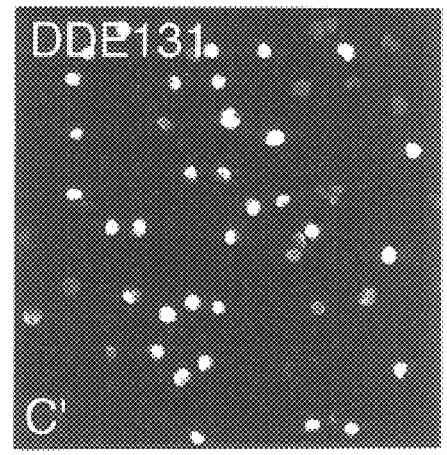

The cytotoxicity of HI-131 against primary cancer cells was evaluated in leukemia cells taken from six children (FIG. 1A), using the MTT assay described for Example 3. The cells were exposed to HI-131 at concentrations ranging from 0 to 50 $\mu$M. Percent survival was calculated as described for Example 3 and plotted against the HI-131 concentration used in the experiment. A composite concentration survival curve was then prepared from the data (FIG. 1B).

The results clearly show a dose dependent cytotoxic effect of HI-131 in primary cancer cells taken from all six patients.

EXAMPLE 5

HI-131 Induces Apoptosis of Leukemia Cells

The ability of HI-131 to induce apoptosis cells was evaluated in human leukemia in NALM-6 cells and primary leukemic cells from 2 patients. Cells were treated with 50 $\mu$M compound HI-131 for 24 hours. After incubation, the cells were harvested and analyzed for apoptosis by in situ TUNNEL analysis and confocal laser scanning microscopy as described in Sudbeck et al., 1999, *Clin Cancer Res.*, 5:1589–82. Controls were treated with vehicle alone.

The data are shown in FIGS. 2A–2F. Controls (FIGS. 2A, 2C, and 2E) failed to induce apoptosis. In contrast treatment with HI-131 (FIGS. 2B, 2D, and 2F) greatly induced apoptosis in the NALM-6 and primary leukemic cells.

Figure 3:
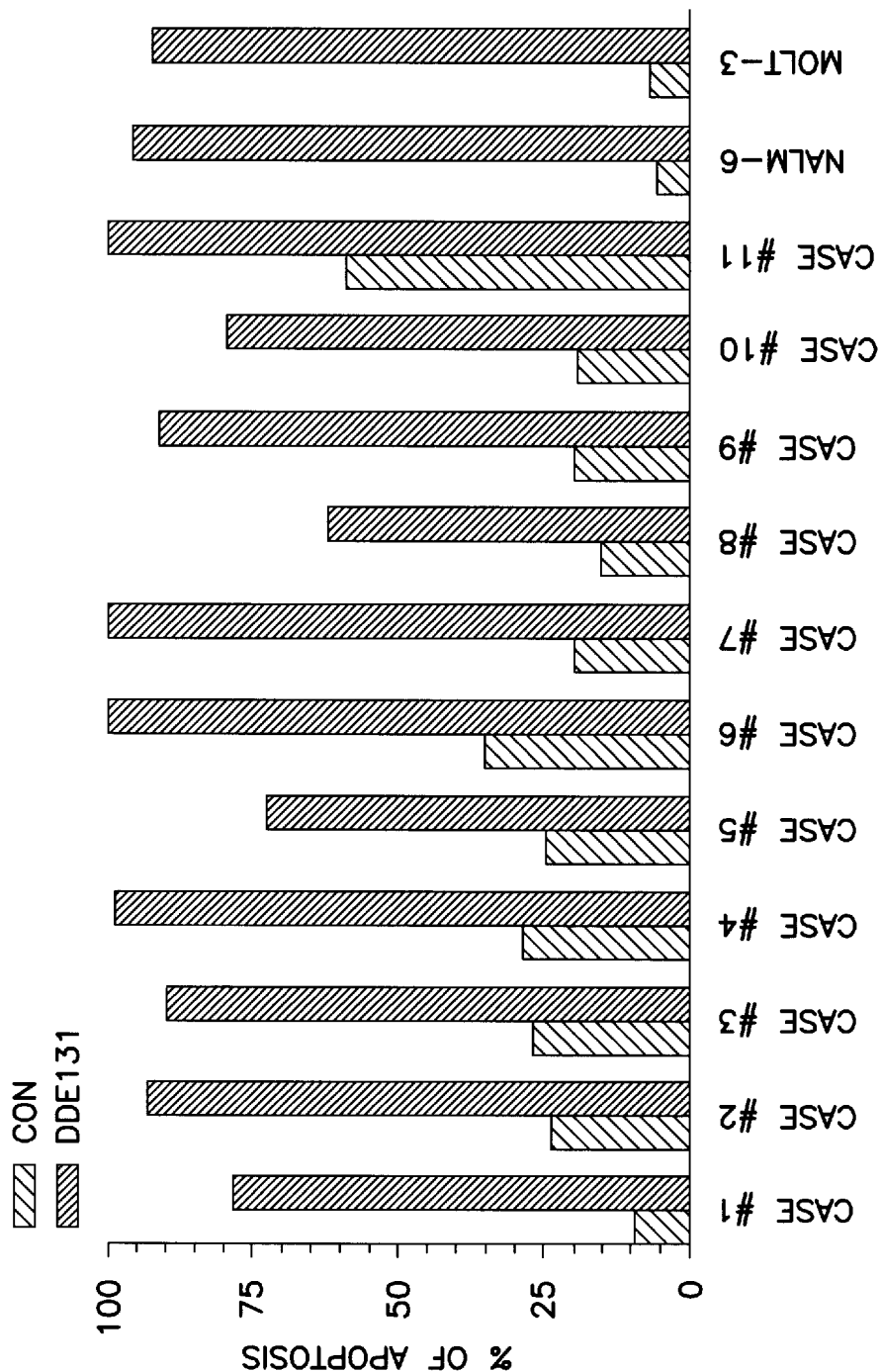
FIG. 3 is a bar graph showing induction of apoptosis by HI-131 in treated primary leukemic cells and established NALM-6 and MOLT-3 cell lines.

Induction of apoptosis was further evaluated in primary leukemic cells and established NALM-6 and MOLT-3 cell lines following treatment with HI-131. Data are shown in FIG. 3.

Primary leukemia cells treated with vehicle alone typically displayed an apoptotic rate of approximately 25%, with one sample exhibiting the much higher rate of about 70%. The rate of apoptosis in the control treated NALM-6 and MOLT-3 cell lines was much lower at about 5%. The rate of apoptosis in all but one of the primary leukemic cell samples increased dramatically after treatment with HI-131 with an approximately 4-fold induction of apoptosis being typical. HI-131, induced apoptosis was much more dramatic in NALM-6 and MOLT-3 cells, with an approximately 20-fold induction of apoptosis.

EXAMPLE 6

HI-131 Inhibits Tumor Cell Invasion

The ability of HI-131 to inhibit invasion by MDA-MB-231 breast cancer cells and U373 glioblastoma cells was evaluated.

Cell Invasion Assay

The in vitro invasiveness of MDA-MB-231 breast cancer cells and U373 glioblastoma cells was assayed using a previously published method which employs Matrigel-coated Costar 24-well transwell cell culture chambers ("Boyden chambers") with 8.0-$\mu$m-pore polycarbonate filter inserts (Albini, et al., 1987, *Cancer Res.*, 47:3239–3245). The chamber filters were coated with 50 $\mu$g/ml of Matrigel matrix, incubated overnight at room temperature under a laminar flow hood and stored at 4° C. Matrigel matrix is made up of several components of the extracellular matrix (ECM), including collagens, laminin and proteo-glycans.

On the day of the experiment, the coated inserts were rehydrated with 0.5 ml serum-free DMEM containing 0.1% bovine serum albumin for 1–2 hours. To study the effects of HI-131 on invasiveness of glioblastoma and breast cancer cells, exponentially growing cells were incubated overnight with HI-131 at various concentrations ranging from 1 $\mu$M to 25 $\mu$M and 2.5 $\mu$M to 25 $\mu$M, respectively. The cells were trypsinized, washed twice with serum-free DMEM containing BSA, counted and resuspended at 1×10$^5$ cells/ml. 0.5 ml cell suspension containing 5×10$^4$ cells in a serum-free DMEM containing HI-131 or vehicle was added to the Matrigel-coated and rehydrated filter inserts. Next, 750 $\mu$l of NIH fibroblast conditioned medium was placed as a chemoattractant in 24-well plates and the inserts were placed in wells and incubated at 37° C. for 48 hours. After the incubation period, the filter inserts were removed, the medium was decanted off and the cells on the top side of the filter that did not migrate were scraped off with a cotton-tipped applicator. The invasive cells that migrated to the lower side of the filter were fixed, stained with Hema-3 solutions and counted under microscope. Five to 10 random fields per filter were counted to determine the mean (SE) values for the invasive fraction. The invasive fractions of cells treated with HI-131 were compared to those of DMSO treated control cells and the percent invading relative to the control was determined using the formula:

$$\% \text{Invading} = 100 * \frac{\text{Number of Adherent Drug Treated Cells}}{\text{Number of Adherent Control Cells}}$$

Each treatment condition was evaluated in duplicate in 3 independent experiments. IC$_{50}$ values were calculated by non-linear regression analysis using Graphpad Prism Software Version 2.0 (Graphpad Software Inc., San Diego, Calif.).

Results

Figure 4:
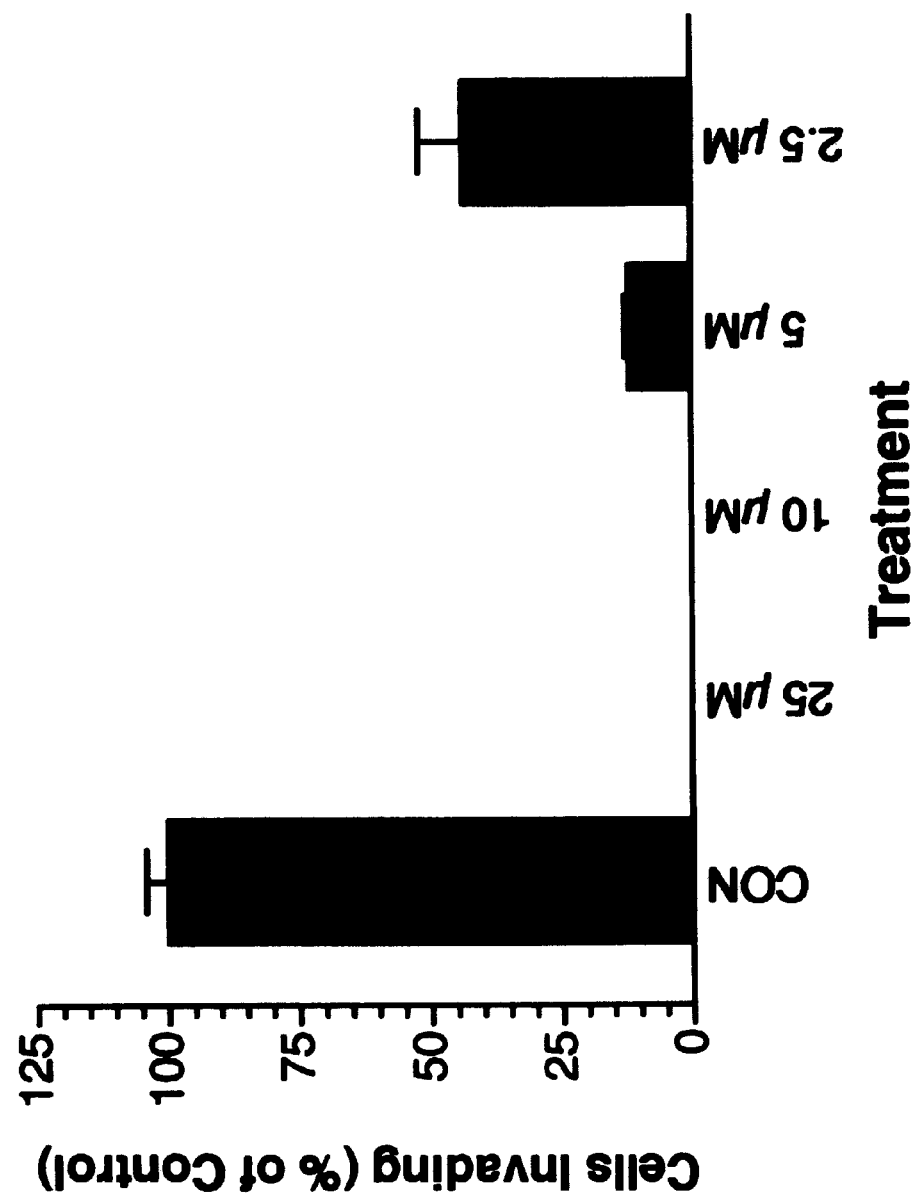
FIG. 4 is a bar graph showing inhibition of invasive properties of human MDA-MB-231 breast cancer cells by HI-131.
Figure 5:
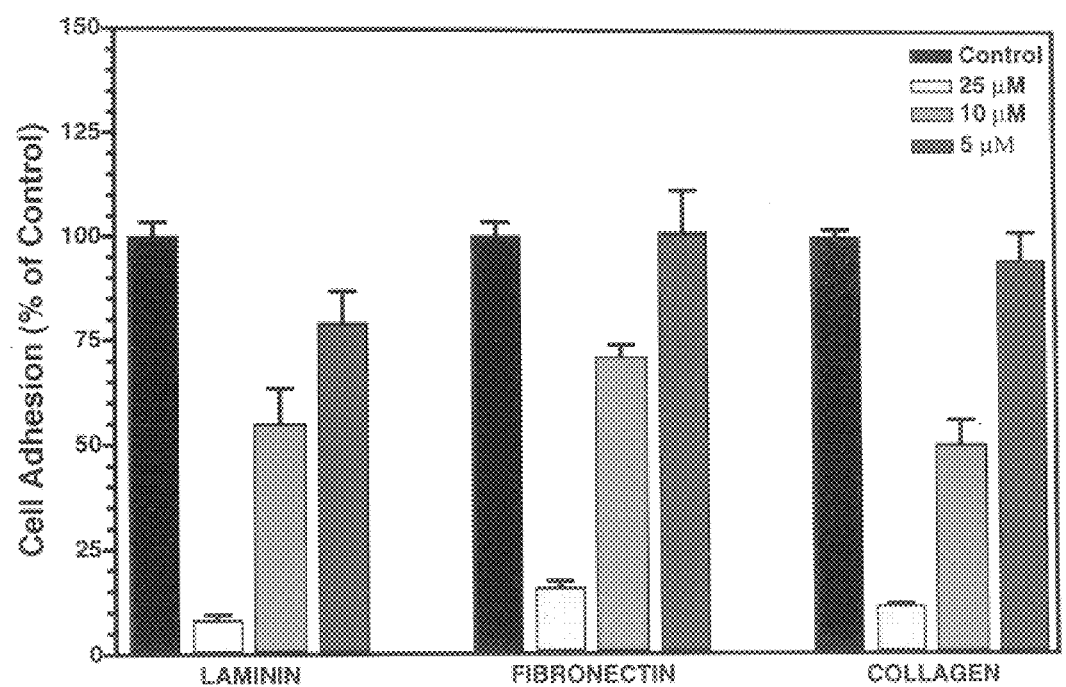
FIG. 5 is a graph showing inhibition of the invasive properties of human U373 (glioblastoma) brain tumor cells by HI-131.

As shown in FIGS. 4 and 5, MDA-MB-231 breast cancer cells and U373 glioblastoma cells were highly invasive in Matrigel-coated Boyden chambers. HI-131 inhibited the invasion of both MDA-MB-231 breast cancer cells and U373 glioblastoma cells through the Matrigel matrix in dose-dependent fashion.

EXAMPLE 7

HI-131 Inhibits Adhesion of Cancer Cells

The ability of HI-131 to inhibit adhesion of MDA-MB-373 and U373 Glioblastoma cells was evaluated.

During the multistep process of tissue invasion, tumor cells initially adhere to the extracellular matrix proteins via cell surface integrin receptors and then gain migratory capacity to enter the surrounding tissues. ECM proteins such as laminin, fibronectin, and type V collagen are thought to play an important role in tumor cell attachment and migration. Laminin, fibronectin and collagen have been found in the basal lamina of blood vessels and in the glial limitans extema in the brain that promote the adhesion and invasion of tumor cells in situ (Carbonetto, 1984, *Trends Neurosci.*, 7:382–387; Rutkaet al. *J. Neurosurg.*, 69:155–170; Venstrom, et al, 1993, *FASEB J.*, 7:996–1003). The effects of these ECM proteins on integrin-mediated U373 glioblastoma and MDA-MB-231 cell adhesion was examined.

Cell Lines

A human brain tumor cell line derived from an adult patient with glioblastoma, U-373 MG (Cat. #HTB-17) and MDA-MB-231 breast cancer cells (Cat. #HTB-26) were obtained from American Type Culture Collection (ATCC, Manassas, Va.) and maintained in liquid culture using DMEM supplemented with 10% fetal bovine serum and antibiotics. Fibroblast conditioned medium was used as a source of chemoattractant in vitro invasion assays. Conditioned medium was prepared as described previously (Albini, et al., 1987, Cancer Res., 47:3239–3245). For the preparation of this conditioned medium NIH/3T3 embryonic fibroblasts (ATCC cat. #CRL-1658) were grown to 80% confluency in DMEM medium supplemented with 10% FBS and cultured for 24 hours in serum-free medium containing 0.5 μg/ml bovine serum albuminutes The culture supernatants were collected, centrifged at 1000× g for 15 minutes to remove cellular debris and used as conditioned medium.

Adhesion Assays

In vitro adhesion assays were performed to (a) study the baseline adhesive properties of U373 glioblastoma and MDA-MB-231 breast cancer cells and (b) evaluate the effects of HI-131 on the adhesive properties of these cells. The plates for the adhesion assays were precoated with the extracellular matrix proteins laminin, fibronectin or type IV collagen (each at a final concentration of 1 μg/ml in PBS) overnight at 4° C. and dried. On the day of the experiment, the wells were rehydrated and blocked with 10% bovine serum albumin in PBS for 1 hour at room temperature and used for the adhesion assays, as described below.

To study the effects of HI-131 on glioblastoma and breast cancer cell adhesion, exponentially growing cells in DMEM were incubated with the compound HI-131 or with genistein at concentrations ranging from 10 μM to 50 μM and 5 μM to 25 μM respectively for 16 hours in a humidified 5% $CO_2$ atmosphere. DMSO (0.1%) was included as a vehicle control. After treatment, cells were detached from the flasks with 0.05% trypsin (Life Technologies) resuspended in DMEM, incubated at 37° C. for 2 hours to allow them to recover from the trypsinization stress and examined for their ability to adhere to plates precoated with ECM proteins.

In adhesion assays, cells were centrifuged, washed twice with serum-free DMEM, counted and resuspended in serum-free DMEM to a final concentration of $2.5 \times 10^5$ cells/ml. One hundred p of the cell suspension containing $2.5 \times 10^4$ cells were added to each well and cells were allowed to adhere for 1 hour at 37° C. in a humidified 5% $CO_2$ atmosphere. The adherent fraction was quantitated using MTT (3-[4,5-dimethylthiazol-2-yl]-2,5-diphenyltetrazolium bromide) assays. In brief, after washing the wells, 10 μl of MTT (0.5 mg/ml final concentration) (Boehringer Mannheim Corp., Indianapolis, Ind.) was added to each well and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 mn and a reference wavelength of 690 nm. To translate the $OD_{540}$ values into the number of cells in each well, the $OD_{540}$ values were compared to those on standard $OD_{540}$-versus-cell number curves generated for each cell line. The adherent fraction of cells treated with HI-131 was compared to the DMSO-treated control cells and the percent adhesion relative to the control was determined.

Each treatment condition was evaluated in duplicate in 3 independent experiments. The $IC_{50}$ values were calculated by non-linear regression analysis.

Results

Figure 6:
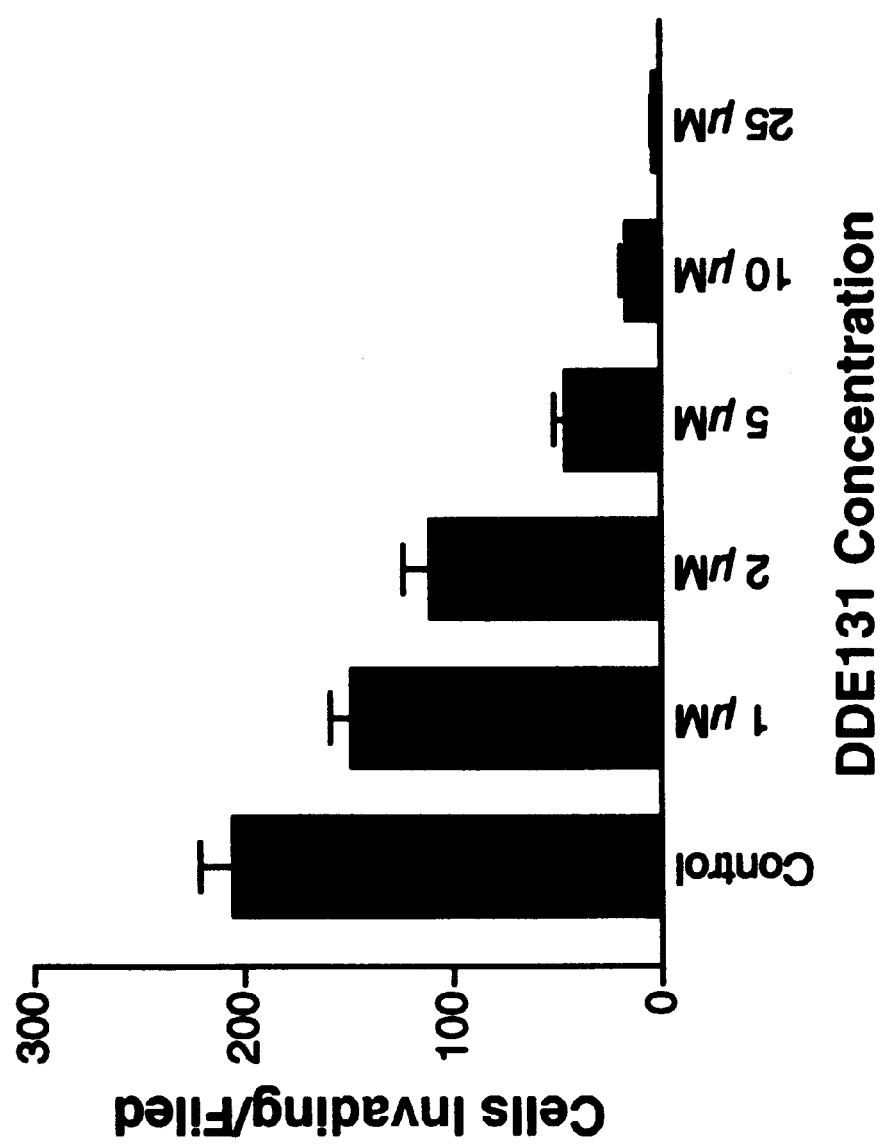
FIG. 6 is a graph showing inhibition of the adhesion of human MDA-MB-231 breast tumor cells by HI-131.
Figure 7:
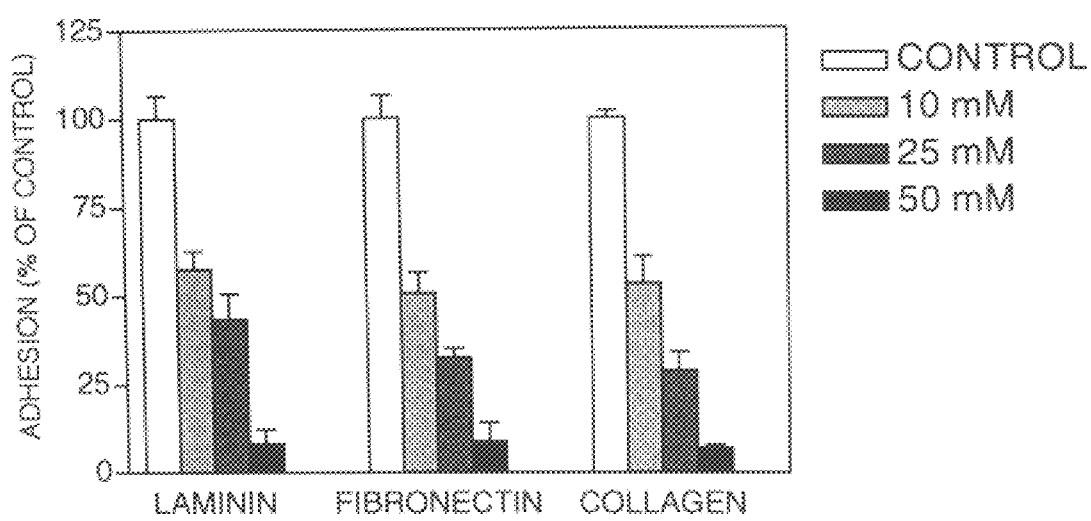
FIG. 7 is a graph showing inhibition of the adhesion by human U373 (glioblastoma) cells by HI-131.

As shown in FIGS. 6 and 7, control U373 glioblastoma cells adhered to plates precoated with laminin, fibronectin, or type IV collagen about equally. Similar results were obtained with MBA-MD-231 breast cancer cells. Treatment with HI-131 resulted in a dose-dependent loss of adhesion in both glioblastoma and breast cells (See FIGS. 6 and 7).

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound of formula II:

(II)

wherein

X is O or S;

$R^1$ ($C_1$–$C_{30}$)haloalkyl or ($C_1$–$C_{30}$) diazoalkyl $R^2$ is ($C_1$–$C_2$)alkylene;

$R^3$ is ($C_1$–$C_{30}$)alkyl, ($C_1$–$C_{30}$) haloalkyl, ($C_1$–$C_{30}$) alkenyl, ($C_1$–$C_{30}$) haloalkenyl, ($C_1$–$C_{24}$)cycloalkyl, ($C_1$–$C_{24}$)cycloalkenyl, ($C_1$–$C_{24}$)aryl, anthroquinonylmethyl, naphthylmethyl, —$SR^{11}$, or —$CH_2R^{12}$;

$R^{11}$ is independently ($C_1$–$C_{30}$)alkyl, ($C_1$–$C_{30}$)haloalkyl, ($C_1$–$C_{30}$)alkenyl, or ($C_1$–$C_{30}$)haloalkenyl;

$R^{12}$ is aryl substituted methyl;

$R^4$ is H, —C(O)$R^{13}$, or —C(O)—O$R^{14}$;

$R^{13}$ and $R^{14}$ are each independently ($C_1$–$C_{12}$)alkyl, ($C_1$–$C_{12}$)haloalkyl, ($C_1$–$C_{12}$)alkenyl, ($C_1$–$C_{12}$) haloalkenyl, ($C_3$–$C_{12}$)cycloalkyl, or ($C_3$–$C_{12}$) cycloalkenyl; or a pharmaceutically acceptable acid addition salt thereof; with the proviso that a compound of formula II excludes N-Boc-S-all-trans-farnesyl-L-cysteine diazomethyl ketone and N-Boc-S-all-trans-farnesyl-L-cysteine chloromethyl ketone.

2. A compound of formula III:

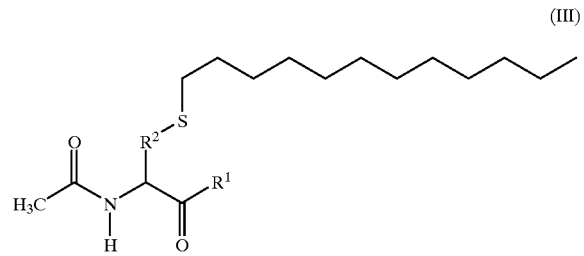

(III)

wherein $R^1$ is ($C_1$–$C_{30}$)haloalkyl or ($C_1$–$C_{30}$)diazoalkyl; and $R^1$ is ($C_1$–$C_2$) alkylene; or a pharmaceutically acceptable acid addition salt thereof.

3. A compound of the formula IV:

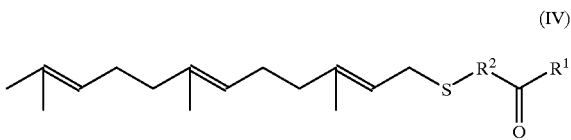

(IV)

wherein
$R^1(C_1-C_{30})$haloalkyl or $(C_1-C_{30})$diazoalkyl; and
$R^2$ is $(C_1-C_2)$ alkylene; or
a pharmaceutically acceptable acid addition salt thereof.

4. The compound of claims 1, 2, or 3, wherein $R^1$ is a $(C_1-C_{30})$chloroalkyl.

5. The compound of claim 4, wherein $R^1$ is chloromethyl or bromomethyl.

6. The compound claims 1, 2 or 3, wherein $R^1$ is $(C_1-C_{30})$ diazoalkyl.

7. The compound of claim 6, wherein $R^1$ is diazomethyl.

8. The compound of claim 1, wherein $R^3$ is $(C_1-C_{30})$ alkyl.

9. A compound of formula II:

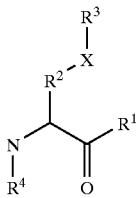

(II)

wherein
X is O or S;
$R^1$ is $(C_1-C_{30})$ haloalkyl or $(C_1-C_{30})$ diazoalkyl
$R^2$ is $(C_1-C_2)$ alkylene;
$R^3$ is $(C_1-C_{30})$ alkyl, $(C_1-C_{30})$ haloalkyl, $(C_1-C_{30})$ alkenyl, $(C_1-C_{30})$ haloalkenyl, $(C_1-C_{24})$ cycloalkyl, $(C_1-C_{24})$ cycloakenyl, $(C_1-C_{24})$ aryl, anthroquinonylmethyl, naphthylmethyl,—$SR^{11}$, or —$CH_2R^{12}$;
$R^{11}$ is independently $(C_1-C_{30})$ alkyl, $(C_1-C_{30})$ haloalkyl, $(C_1-C_{30})$ alkenyl, or $(C_1-C_{30})$ haloalkenyl;
$R^{12}$ is aryl substituted methyl;
$R^4$ is acetyl, BOC, or BOC-amino acid; or a pharmaceutically acceptable acid addition salt thereof.

10. The compound of claim 9, wherein said amino acid is Glycine.

11. The compound of claim 2, wherein $R^{13}$ is methyl or ethyl.

12. The compound of claim 1, wherein $R^1$ is $(C_1-C_{30})$ haloalkyl, $R^2$ is $(C_1-C_2)$ alkylene, $R^3$ is $(C_1-C_{30})$ alkyl, and $R^4$ is -$COCH_3$.

13. The compound of claim 12, wherein $R^1$ is chloroalkyl or bromoalkyl.

14. The compound of claim 12, wherein $R^1$ is chloromethyl or bromomethyl.

15. The compound of claim 12, wherein $R^3$ is $(C_{12})$ alkyl.

16. The compound of claim 12, having the structure of N-Ac-S-dodecyl-cys chloromethyl ketone (HI-131); or a pharmaceutically acceptable addition salt thereof.

17. A pharmaceutical composition comprising a therapeutically effective amount of a compound of claims 1, 2 or 3 and a pharmaceutically acceptable carrier or diluent.

18. A method for inducing apoptosis of tumor cells in a subject comprising administering to said subject a compound of claims 1, 2 or 3.

19. A method of treating leukemia breast cancer, prostate cancer, or brain tumor in a subject comprising administering to said subject a compound of claims 1, 2 or 3.

20. A method for inducing cytotoxicity in a cancer cell comprising: administering to said cell a cytotoxic dose of the compound of claims 1, 2 or 3.

21. A method of treating leukemia, breast cancer, prostate cancer, or brain tumor in a subject comprising administering to said subject a compound selected from the group consisting of:
N-Ac-S-trans-trans-farnesyl-Cys diazomethyl ketone (HI-367);
N-Ac-S-trans-trans-farnesyl-Cys chloromethyl ketone (HI-368);
N-Ac-S-trans-geranyl-Cys diazomethyl ketone (HI-122);
N-Ac-S-trans-geranyl-Cys chloromethyl ketone (HI-127);
N-Ac-S-(3-methyl-2-butenyl)Cys diazomethyl ketone (HI-123);
N-Ac-S-(3-methyl-2-butenyl)Cys chloromethyl ketone (HI-28);
N-Ac-S-dodecyl-Cys diazomethyl ketone (HI-348);
N-Ac-S-dodecyl-Cys chloromethyl ketone (HI-131);
N-Boc-S-farnesyl-Cys diazomethyl ketone (HI-82);
N-Boc-S-farnesyl-Cys chloromethyl ketone (HI-124);
S-trans-trans-Farnesyl-mercaptoethyl diazomethyl ketone (HI-83);
S-trans-trans-Farnesyl-2-mercaptoethyl chloromethyl ketone (HI-125);
S-trans-trans-Farnesyl-mercaptomethyl diazomethyl ketone (HI-84);
S-trans-trans-Farnesyl-mercaptomethyl chloromethyl ketone (HI-126);
N-Boc-S-dodecyl-Cys chloromethyl ketone (HI-129);
S-Dodecyl-Cys chloromethyl ketone hydrochloride (HI-252);
N-Boc-Gly-S-trans- trans-farnesyl-Cys diazomethyl ketone (HI-401);
N-Boc-Gly-S-trans-trans-farnesyl-Cys chloromethyl ketone (HI-130);
N-Ac-S-methyl-cysteine chloromethyl ketone (HI-314);
N-Ac-S-ethyl-cysteine chloromethyl ketone (HI-315);
N-Ac-S-propyl-cysteine chloromethyl ketone (HI-369);
N-Ac-S-butyl-cysteine chloromethyl ketone (HI-363);
N-Ac-S-pentyl-cysteine chloromethyl ketone (HI-224);
N-Ac-S-hexyl-cysteine chloromethyl ketone (HI-357);
N-Ac-S-heptyl-cysteine chloromethyl ketone (HI-263);
N-Ac-S-octyl-cysteine chloromethyl ketone (HI-352);
N-Ac-S-nonyl-cysteine chloromethyl ketone (HI-364);
N-Ac-S-decyl-cysteine chloromethyl ketone (HI-371);
N-Ac-S-undecyl-cysteine chloromethyl ketone (HI-321);
N-Ac-S-tridecyl-cysteine chloromethyl ketone (HI-323);
N-Ac-S-tetradecyl-cysteine chloromethyl ketone (HI-354);
N-Ac-S-pentadecyl-cysteine chloromethyl ketone (HI-225);
N-Ac-S-hexadecyl-cysteine chloromethyl ketone (HI-366);
N-Ac-S-octadecyl-cysteine chloromethyl ketone (HI-370);
N-Ac-S-eicoyl-cysteine chloromethyl ketone (HI-226);
N-Ac-S-docosyl-cysteine chloromethyl ketone (HI-322);
N-Ac-S-allyl-cysteine chloromethyl ketone (HI-419);
N-Ac-S-t-butyl-cysteine chloromethyl ketone (HI-349);
N-Ac-S-2-methylpropyl-cysteine chloromethyl ketone (HI-391);
N-Ac-S-2,2-dimethylpropyl-cysteine chloromethyl ketone (HI-421);
N-Ac-S-3-methylbutyl-cysteine chloromethyl ketone (HI-387);

N-Ac-S-2-ethylbutyl-cysteine chloromethyl ketone (HI-390);
N-Ac-S-cyclopropylmethyl-cysteine chloromethyl ketone (HI-507);
N-Ac-S-cyclobutylmethyl-cysteine chloromethyl ketone (HI-385);
N-Ac-S-cyclohexylmethyl-cysteine chloromethyl ketone (HI-386);
N-Ac-S-benzyl-cysteine chloromethyl ketone (HI-251);
N-Ac-S-4-methoxybenzyl-cysteine chloromethyl ketone (HI-349);
N-Ac-S-benzyloxycarbonyl-cysteine chloromethyl ketone (HI-389);
N-Ac-S-diphenylmethyl-cysteine chloromethyl ketone (HI-418);
N-Ac-S-trityl-cysteine chloromethyl ketone (HI-350);
N-Ac-S-2-naphthylmethyl-cysteine chloromethyl ketone (HI-392);
N-Ac-0dodecyl-serine chloromethyl ketone (HI-489);
N-Boc-O-dodecyl serine chloromethyl ketone (HI-266);
N-Propyloxycarbonyl-S-dodecyl-cysteine chloromethyl ketone (HI-413);
N-Benzyloxycarbonyl-S-dodecyl-cysteine chloromethyl ketone (HI-320);
N-9-Fluorenylmethyloxycarbonyl-S-dodecyl-cysteine chloromethyl ketone (HI-398);
N-3-Dimethylaminobenzoyl-S-dodecyl-cysteine chloromethyl ketone (HI-268);
N-Ac-S-dodecyl-cysteine bromomethyl ketone (HI-488);
N-Ac-S-dodecyl-Cys-H (HI-274);
N-Ac-S-dodecyl-Cys-CH$_2$-SPh (HI-269);
N-Ac-S-dodecyl-Cys-CH$_2$-S-2-naphthyl (HI-302); and
N-Ac-S-dodecyl-Cys-CH$_2$-S-CH$_2$CH$_2$CO$_2$H (HI-273).

22. A compound selected from the group consisting of:
N-Ac-S-trans-trans-farnesyl-Cys diazomethyl ketone (HI-367);
N-Ac-S-trans-trans-farnesyl-Cys chloromethyl ketone (HI-368);
N-Ac-S-trans-geranyl-Cys diazomethyl ketone (HI-122);
N-Ac-S-trans-geranyl-Cys chloromethyl ketone (HI-127);
N-Ac-S-(3-methyl-2-butenyl)Cys diazomethyl ketone (HI-123);
N-Ac-S-(3-methyl-2-butenyl)-Cys chloromethyl ketone (HI-128);
N-Ac-S-dodecyl-Cys diazomethyl ketone (HI-348);
N-Ac-S-dodecyl-Cys chloromethyl ketone (HI-131);
S-trans-trans-Farnesyl-mercaptoethyl diazomethyl ketone (HI-83);
S-trans-trans-Farnesyl-2-mercaptoethyl chloromethyl ketone (HI-125);
S-trans-trans-Farnesyl-mercaptomethyl diazomethyl ketone (HI-84);
S-trans-trans-Farnesyl-mercaptomethyl chloromethyl ketone (HI-126);
N-Boc-S-dodecyl-Cys chloromethyl ketone (HI-129);
S-Dodecyl-Cys chloromethyl ketone hydrochloride (HI-252);
N-Boc-Gly-S-trans-trans-farnesyl-Cys diazomethyl ketone (HI-401);
N-Boc-Gly-S-trans-trans-farnesyl-Cys chloromethyl ketone (HI-130);
N-Ac-S-methyl-cysteine chloromethyl ketone (HI-314);
N-Ac-S-ethyl-cysteine chloromethyl ketone (HI-315);
N-Ac-S-propyl-cysteine chloromethyl ketone (HI-369);
N-Ac-S-butyl-cysteine chloromethyl ketone (HI-363);
N-Ac-S-pentyl-cysteine chloromethyl ketone (HI-224);
N-Ac-S-hexyl-cysteine chloromethyl ketone (HI-357);
N-Ac-S-heptyl-cysteine chloromethyl ketone (HI-263);
N-Ac-S-octyl-cysteine chloromethyl ketone (HI-352);
N-Ac-S-nonyl-cysteine chloromethyl ketone (HI-364);
N-Ac-S-decyl-cysteine chloromethyl ketone (HI-371);
N-Ac-S-undecyl-cysteine chloromethyl ketone (HI-321);
N-Ac-S-tridecyl-cysteine chloromethyl ketone (HI-323);
N-Ac-S-tetradecyl-cysteine chloromethyl ketone (HI-354);
N-Ac-S-pentadecyl-cysteine chloromethyl ketone (HI-225);
N-Ac-S-hexadecyl-cysteine chloromethyl ketone (HI-366);
N-Ac-S-octadecyl-cysteine chloromethyl ketone (HI-370);
N-Ac-S-eicoyl-cysteine chloromethyl ketone (HI-226);
N-Ac-S-docosyl-cysteine chloromethyl ketone (HI-322);
N-Ac-S-allyl-cysteine chloromethyl ketone (HI-419);
N-Ac-S-t-butyl-cysteine chloromethyl ketone (HI-349);
N-Ac-S-2-methylpropyl-cysteine chloromethyl ketone (HI-391);
N-Ac-S-2,2-dimethylpropyl-cysteine chloromethyl ketone (HI-421);
N-Ac-S-3-methylbutyl-cysteine chloromethyl ketone (HI-387);
N-Ac-S-2-ethylbutyl-cysteine chloromethyl ketone (HI-390);
N-Ac-S-cyclopropylmethyl-cysteine chloromethyl ketone (HI-507);
N-Ac-S-cyclobutylmethyl-cysteine chloromethyl ketone (HI-385);
N-Ac-S-cyclohexylmethyl-cysteine chloromethyl ketone (HI-386);
N-Ac-S-benzyl-cysteine chloromethyl ketone (HI-251);
N-Ac-S-4-methoxybenzyl-cysteine chloromethyl ketone (HI-349);
N-Ac-S-benzyloxycarbonyl-cysteine chloromethyl ketone (HI-389);
N-Ac-S-diphenylmethyl-cysteine chloromethyl ketone (HI-418);
N-Ac-S-trityl-cysteine chloromethyl ketone (HI-350);
N-Ac-S-2-naphthylmethyl-cysteine chloromethyl ketone (HI-392);
N-Ac-O-dodecyl-serine chloromethyl ketone (HI-489);
N-Boc-O-dodecyl serine chloromethyl ketone (HI-266);
N-Propyloxycarbonyl-S-dodecyl-cysteine chloromethyl ketone (HI-413);
N-Benzyloxycarbonyl-S-dodecyl-cysteine chloromethyl ketone (HI-320);
N-9-Fluorenylmethyloxycarbonyl-S-dodecyl-cysteine chloromethyl ketone (HI-398);
N-3-Dimethylaminobenzoyl-S-dodecyl-cysteine chloromethyl ketone (HI-268);
N-Ac-S-dodecyl-cysteine bromomethyl ketone (HI-488);
N-Ac-S-dodecyl-Cys-H (HI-274);
N-Ac-S-dodecyl-Cys-CH$_2$-SPh (HI-269);
N-Ac-S-dodecyl-Cys-CH$_2$-S-2-naphthyl (HI-302); and
N-Ac-S-dodecyl-Cys-CCH$_2$-S-CH$_2$CH$_2$CO$_2$H (HI-273).

\* \* \* \* \*